United States Patent
Ishikawa et al.

(10) Patent No.: US 9,458,513 B2
(45) Date of Patent: Oct. 4, 2016

(54) PRIMER AND PROBE FOR DETECTING CHLAMYDIA TRACHOMATIS, AND METHOD FOR DETECTING CHLAMYDIA TRACHOMATIS USING SAME

(75) Inventors: Tomokazu Ishikawa, Hyogo (JP); Hiromi Kumon, Okayama (JP)

(73) Assignee: WAKO PURE CHEMICAL INDUSTRIES, LTD., Osaka (JP)

( * ) Notice: Subject to any disclaimer, the term of this patent is extended or adjusted under 35 U.S.C. 154(b) by 426 days.

(21) Appl. No.: 13/636,250

(22) PCT Filed: Mar. 17, 2011

(86) PCT No.: PCT/JP2011/056378
§ 371 (c)(1),
(2), (4) Date: Nov. 15, 2012

(87) PCT Pub. No.: WO2011/118496
PCT Pub. Date: Sep. 29, 2011

(65) Prior Publication Data
US 2013/0059306 A1    Mar. 7, 2013

(30) Foreign Application Priority Data
Mar. 23, 2010 (JP) ................................ 2010-065560

(51) Int. Cl.
C12Q 1/68 (2006.01)
C07H 21/04 (2006.01)

(52) U.S. Cl.
CPC ..................................... *C12Q 1/689* (2013.01)

(58) Field of Classification Search
None
See application file for complete search history.

(56) References Cited

U.S. PATENT DOCUMENTS

| 5,232,829 | A | 8/1993 | Longiaru et al. |
| 5,814,490 | A | 9/1998 | Spears |
| 6,096,501 | A | 8/2000 | Foxall et al. |
| 6,218,125 | B1 | 4/2001 | Foxall et al. |
| 7,384,638 | B2 * | 6/2008 | Bhatia et al. ............. 424/192.1 |
| 2010/0248220 | A1 | 9/2010 | Ku et al. |

FOREIGN PATENT DOCUMENTS

| CA | 2354232 A1 | 6/2000 |
| CA | 2746535 A1 | 6/2000 |
| CA | 2390088 A1 | 6/2001 |
| CA | 2418282 A1 | 1/2002 |
| CN | 1333832 A | 1/2002 |
| CN | 101363041 A | 2/2009 |

(Continued)

OTHER PUBLICATIONS

Moller, J.K. et al. Journal of Clinical Microbiology 46(12):3892 (Dec. 2008).*

(Continued)

*Primary Examiner* — Diana B Johannsen
(74) *Attorney, Agent, or Firm* — Finnegan, Henderson, Farabow, Garrett & Dunner LLP

(57) ABSTRACT

The present invention relates to an oligonucleotide which is designed on the basis of a nucleotide sequence shown in SEQ ID NO: 1 or SEQ ID NO: 2 and hybridizes with the endogenous plasmid gene of *Chlamydia trachomatis*, oligonucleotide primer and probe for detecting *Chlamydia trachomatis*, the detection method of *Chlamydia trachomatis* using said primer and probe, and a primer for detecting *Chlamydia trachomatis* of said oligonucleotide or the use to a probe design.

7 Claims, 2 Drawing Sheets

(56) References Cited

FOREIGN PATENT DOCUMENTS

| EP | 0915170 A1 | 5/1999 |
|---|---|---|
| JP | 2719225 | 11/1997 |
| JP | 3127135 | 11/2000 |
| WO | WO 9947706 A1 * | 9/1999 |
| WO | WO 2007/056398 A2 | 5/2007 |

OTHER PUBLICATIONS

Ma, H. et al. Journal of American Science 2(3):1 (2006).*
Ohio State University (OSU), "Procedures and Recommendations for Quantitative PCR", version 1.2 (Apr. 2003).*
Sigma qPCR Technical Guide (42 pages), Sigma Life Science (2008).*
Warren et al.; "Comparative Evaluation of Detection Assays for *Chlamydia trachomatis*", Journal of Clinical Microbiology, vol. 31, No. 6, pp. 1663-1666, (1993).
Domeika et al.; "Diagnosis of Genital *Chlamydia trachomatis* Infections in Asymptomatic Males by Testing Urine by PCR", Journal of Clinical Microbiology, vol. 32, No. 10, pp. 2350-2352, (1994).
Bauwens et al.; "Diagnosis of *Chlamydia trachomatis* Urethritis in Men by Polymerase Chain Reaction Assay of First-Catch Urine", Journal of Clinical Microbiology, vol. 31, No. 11, pp. 3013-3016, (1993).
Chernesky et al.; "Diagnosis of *Chlamydia trachomatis* Infections in Men and Women by Testing First-Void Urine by Ligase Chain Reaction", Journal of Clinical Microbiology, vol. 32, No. 11, pp. 2682-2685, (1994).
Lee et al.; "Diagnosis of *Chlamydia trachomatis* Genitourinary Infection in Women by Ligase Chain Reaction Assay of Urine", The Lancet, vol. 345, pp. 213-216, (1995).
Bassiri et al.; "Detection of *Chlamydia trachomatis* in Urine Specimens From Women by Ligase Chain Reaction", Journal of Clinical Microbiology, vol. 33, No. 4, pp. 898-900, (1995).
Hatt et al.; "Analysis of the Entire Nucleotide Sequence of the Cryptic Plasmid of *Chlamydia trachomatis* Serovar L1. Evidence for Involvement in DNA Replication", Nucleic Acids Research, vol. 16, No. 9, pp. 4053-4067, (1988).
Herrmann et al.; "Emergence and Spread of *Chlamydia trachomatis* Variant, Sweden", Emerging Infectious Diseases, vol. 14, No. 9, pp. 1462-1465, (2008).
English-Language International Search Report from the Japanese Patent Office for International Application No. PCT/JP2011/056378, mailing date May 10, 2011.
PCT/IB/338, enclosing English translation of PCT/IB/373, International Preliminary Report on Patentability for PCT/JP2011/056378, mailed Oct. 26, 2012 (7 pages).
Extended European Search Report for European Application No. 11759302.0, mailed Aug. 6, 2013.
Keegan et al., "Comparison of DNA extraction from cervical cells collected in PreservCyt solution for the amplification of *Chlamydia trachomatis*," *Cytopathology*, 16: 82-87 (2005).
Little, M.C. et al., "Strand Displacement Amplification and Homogeneous Real-Time Detection Incorporated in a Second-Generation DNA Probe System, BDProbe TecET," *Clinical Chemistry*, vol. 45, No. 6, p. 777-784 (1999).

* cited by examiner

PRIMER AND PROBE FOR DETECTING CHLAMYDIA TRACHOMATIS, AND METHOD FOR DETECTING CHLAMYDIA TRACHOMATIS USING SAME

RELATED APPLICATIONS

This application is the national stage of International Application No. PCT/JP2011/056378, filed Mar. 17, 2011, which claims the benefit Japanese Application No. JP2010/065560, filed Mar. 23, 2010, which are both incorporated herein by reference.

TECHNICAL FIELD

The present invention relates to a method for detecting and/or identifying *Chlamydia trachomatis* utilized nucleic acid amplification and detection system thereof.

BACKGROUND ART

In concurrence with diversification of the sexual manners and customs and change in pattern of sexual behavior of the Japanese centering on the young people, an increase in the chlamydial infection as a sexually transmitted disease is significant today.

*Chlamydia* is an obligate intracellular parasitic bacterium of eukaryotic cell. *Chlamydia* grows and proliferates in a host cell, and forms an inclusion in the cytoplasm of the cell, and this causes clinical symptoms to the host. For example, the causative microorganism of genital chlamydial infection is *Chlamydia trachomatis*, which mainly develops the symptoms of urethritis in a man and cervicitis in a woman.

As a detection method of chlamydia, methods for detecting antigen, such as direct fluorescent antibody staining (DFA), enzyme immunoassay (EIA), and enzyme linked immunosorbent assay (ELISA), have been developed. In addition, a detection method for detecting *Chlamydia trachomatis* by probe hybridization technique using labeling substance-labeled single-stranded DNA which is complementary to the ribosomal RNA of *Chlamydia trachomatis* has also been developed (Gen-Probe Pace 2 *Chlamydia* test, Non-patent Literature 1).

Furthermore, a higher sensitive detection method utilized nucleic acid amplification technique has also been developed.

For example, Domeika et al. (Non-patent Literature 2), Bauwens et al. (Non-patent Literature 3), and specification of U.S. Pat. No. 5,232,829 (Patent Literature 1) have reported a method for detecting *Chlamydia trachomatis* by performing polymerase chain reaction (PCR) and subsequent microtitration plate hybridization.

In addition, a method for detecting *Chlamydia trachomatis* by performing ligase chain reaction (LCR) and subsequent microparticle sandwich immunoassay detection has also been reported (Non-patent Literature 4, Non-patent Literature 5 and Non-patent Literature 6).

Further, it has been known that *Chlamydia trachomatis* has multiple copies of endogenous plasmid specific for this bacterium (Non-patent Literature 7). And, a method for detecting *Chlamydia trachomatis* by using a particular sequence of this endogenous plasmid as a target, amplifying a part of the sequence thereof by a gene amplification method, and detecting the amplification products has been developed (Patent Literature 2, Patent Literature 3).

By the way, it has been known that there are 18 kinds of serologic type which were identified immunologically for *Chlamydia trachomatis*. And, in recent years, a case where *Chlamydia trachomatis* could not be detected by the above-described conventional detection method of *Chlamydia trachomatis* has been reported (Non-patent Literature 8). That is, it turned out that by the conventional detection method of *Chlamydia trachomatis*, there may be a case of providing a false negative detection, and it has been a problem.

CITATION LIST

Patent Literature

Patent Literature 1: U.S. Pat. No. 5,232,829;
Patent Literature 2: JP-B-2719225;
Patent Literature 2: JP-B-3127135;

Non-Patent Literature

Non-patent Literature 1: Warren R., et al., Journal of Clinical Microbiology, 1993, 31, 1663-1666;
Non-patent Literature 2: Domeika M. et al., Journal of Clinical Microbiology, 1994, 32, 2350-2352;
Non-patent Literature 3: Bauwens J. E. et al., Journal of Clinical Microbiology, 1993, 31, 3013-3106;
Non-patent Literature 4: Chernesky Max A. et al., Journal of Clinical Microbiology, 1994, 32, 2682-2685;
Non-patent Literature 5: Lee H. H. et al., Lancet, 1995, 345, 213-216;
Non-patent Literature 6: Bassiri M. et al., Journal of Clinical Microbiology, 1995, 33, 898-900;
Non-patent Literature 7: C. Hatt et al., Nucleic Acid Research, 1988, 16(9), p. 4053-4067;
Non-patent Literature 8: Emerging Infectious Diseases Vol. 14, No. 9, September 2008.

SUMMARY OF INVENTION

Problem to be Solved by the Invention

The present invention was made in view of the above-described situation, and it is an object of the present invention to provide a detection method of *Chlamydia trachomatis* which does not give rise to any false negative determination, and has excellent sensitivity and specificity as well as rapid performance.

Means for Solving the Problem

The present invention was made for the purpose of solving the above-described problems, and made up of the following constituents,
(1) An oligonucleotide designed on the basis of a nucleotide sequence shown in SEQ ID NO: 1 or SEQ ID NO: 2 and being capable of hybridizing with an endogenous plasmid gene of *Chlamydia trachomatis*,
(2) An oligonucleotide primer designed on the basis of the nucleotide sequence shown in SEQ ID NO: 1 or SEQ ID NO: 2 and being capable of hybridizing with an endogenous plasmid gene of *Chlamydia trachomatis*,
(3) An oligonucleotide probe designed on the basis of the nucleotide sequence shown in SEQ ID NO: 1 or SEQ ID NO: 2 and being capable of hybridizing with an endogenous plasmid gene of *Chlamydia trachomatis*,
(4) A method for detecting *Chlamydia trachomatis* characterized in that by setting a region of nucleotide No. 4133 to nucleotide No. 4277 having a nucleotide sequence shown in SEQ ID NO: 1 or a region of nucleotide No. 32 to nucleotide No. 176 having a nucleotide sequence shown in SEQ ID NO: 2, or a further particular region within these regions, in the endogenous plasmid gene of *Chlamydia trachomatis* shown in SEQ ID NO: 10, as a target, and comprising performing a nucleic acid amplification reaction using an oligonucleotide designed on the basis of the nucleotide sequence shown in SEQ ID NO: 1 or SEQ ID NO: 2 and being capable of hybridizing with the endogenous plasmid gene of *Chlamydia trachomatis* as a primer, and using nucleic acid in a sample as a template, and detecting the resulting product obtained by the reaction in order to confirm whether the oligonucleotide having a nucleotide sequence of these region exists or not in a sample, (5) A reagent kit for detecting *Chlamydia trachomatis* comprising an oligonucleotide designed on the basis of the nucleotide sequence shown in SEQ ID NO: 1 or SEQ ID NO: 2 and being capable of hybridizing with an endogenous plasmid gene of *Chlamydia trachomatis* as a primer and/or a probe.

The present inventors have conducted theoretical verification and experimental verification of homology of each gene sequence of between each species regarding *Chlamydia trachomatis* determined up to now and other living organisms. As a result, the present inventors have obtained nucleotide sequence most suitable for detection of *Chlamydia trachomatis*, and further, on the basis of these sequences, have developed a primer and a probe for the detection of *Chlamydia trachomatis*, and has established a detection method of *Chlamydia trachomatis* using these, and thus completed the present invention.

EFFECT OF THE INVENTION

According to the present invention, a method having excellent sensitivity and specificity and rapidity for detection of *Chlamydia trachomatis* is provided. In addition, by the detection method which uses the primer for detection provided by the present invention, any false negative result which comes out potentially by the conventional method can be avoided, and detection of *Chlamydia trachomatis* can be performed with high accuracy.

EMBODIMENTS FOR CARRYING OUT THE INVENTION

The present inventors have focused their attention on a plasmid called pLGV440 as an endogenous plasmid of *Chlamydia trachomatis*.

Figure 2:
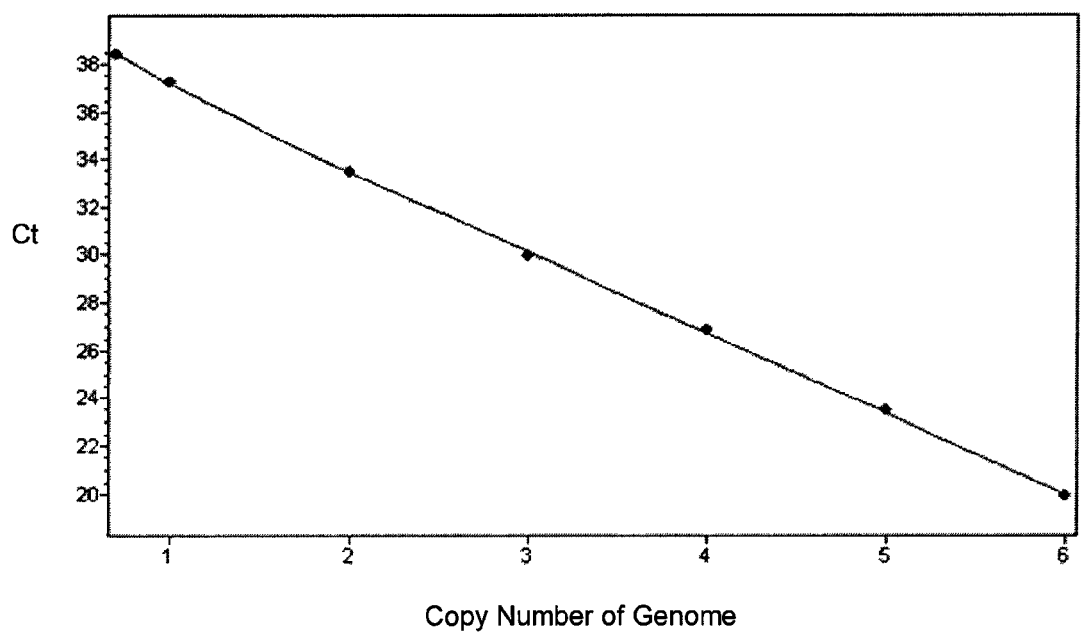
FIG. 2 shows a calibration curve made up on the basis of the amplification curve obtained by the real time PCR performed in Example 2, by plotting Ct value (y-axis) for the copy number of genome (x-axis, logarithmic scale).

The entire nucleotide sequence of the endogenous plasmid (cryptic plasmid) pLGV440 in *Chlamydia trachomatis* has been described in FIG. 2 of Non-patent Literature 7, which has 7498 nucleotides in size and a nucleotide sequence shown in SEQ ID NO: 10 in the present description.

In the present invention, when described as "endogenous plasmid gene of *Chlamydia trachomatis*", there may be a case where it refers to the entire nucleotide sequence of the above-described endogenous plasmid gene (pLGV440) of *Chlamydia trachomatis* and a case where it refers to an optional nucleotide sequence unit (region) within said entire nucleotide sequence. In addition, "the endogenous plasmid in *Chlamydia trachomatis*" is sometimes referred to simply as "endogenous plasmid", hereinafter.

The present inventors noticed two particular regions in the endogenous plasmid gene (pLGV440). That is, those are a region from nucleotide No. 4133 to nucleotide No. 4277 (consisting of a nucleotide sequence shown in SEQ ID NO: 1) of the endogenous plasmid gene (pLGV440) of *Chlamydia trachomatis* shown in SEQ ID NO: 10, and a region from nucleotide No. 32 to nucleotide No. 176 (consisting of a nucleotide sequence shown in SEQ ID NO: 2) of the endogenous plasmid gene (pLGV440) of *Chlamydia trachomatis* shown in SEQ ID NO: 10. The present inventors gave a name of "TcTI_Fw01Rv01" to the nucleotide sequence shown in SEQ ID NO: 1, and gave a name of "TcTI_Fw02Rv02" to the nucleotide sequence shown in SEQ ID NO: 2.

And, on the basis of the nucleotide sequence of these two regions, the oligonucleotide of the present invention, which can be used for the detection of *Chlamydia trachomatis*, was designed.

That is, the oligonucleotide of the present invention is "an oligonucleotide designed on the basis of the nucleotide sequence shown in SEQ ID NO: 1 or SEQ ID NO: 2 and being capable of hybridizing with the endogenous plasmid gene of *Chlamydia trachomatis*" (hereinafter, sometimes abbreviated to "the oligonucleotide of the present invention").

A specific example of "the oligonucleotide designed on the basis of the nucleotide sequence shown in SEQ ID NO: 1 or SEQ ID NO: 2" of the present invention includes "the oligonucleotide comprising a nucleotide sequence shown in any one of SEQ ID NO: 1 to SEQ ID NO: 9, or the sequence complementary to the nucleotide sequence shown in any one of SEQ ID NO: 1 to SEQ ID NO: 9" of sequence listing.

As "a sequence complementary to the nucleotide sequence shown in any one of SEQ ID NO: 1 to SEQ ID NO: 9" of the present invention includes, for example, and an oligonucleotide comprising a nucleotide sequence capable of hybridizing with an oligonucleotide comprising a nucleotide sequence shown in any one of SEQ ID NO: 1 to SEQ ID NO: 9 of the present invention under stringent condition or high stringent condition.

The term "stringent condition" as used herein means, specifically, for example, the condition where "hybridization is performed in 6×SSC or a hybridization solution of equivalent salt concentration at temperature of 50° C. to 70° C. for 16 hours, and then, if needed, pre-washing with 6×SSC or a hybridization solution of equivalent salt concentration, and followed by washing with 1×SSC or a solution of equivalent salt concentration and the like".

The term "high stringent condition" as used herein means, specifically, for example, the condition where "hybridization is performed in 50% formamide at 42° C. to 70° C., preferably 60° C. to 70° C., and followed by washing in 0.2 to 2×SSC, 0.1% sodium dodecyl sulfate (SDS) at 25° C. to 70°C".

For example, in the method for detecting *Chlamydia trachomatis* using a nucleic acid amplification reaction such as polymerase chain reaction (PCR), a nucleotide sequence of a specified region of the gene for *Chlamydia trachomatis* is set as a target, then the PCR is performed using a primer set which can amplify the nucleotide sequence, and using nucleic acid in the sample as a template. And, when the objective primer extension product is obtained, it is determined as a nucleic acid having the target nucleotide sequence is present in the sample. Namely, it can be determined that *Chlamydia trachomatis* or its gene is present.

The nucleotide sequence shown in SEQ ID NO: 1 or SEQ ID NO: 2 of the present invention, or a sequence complementary to the nucleotide sequence shown in SEQ ID NO: 1 or SEQ ID NO: 2 can be a target for the above-described detection of *Chlamydia trachomatis*.

In more specific explanation, the PCR is performed targeting the nucleotide sequence shown in SEQ ID NO: 1 or SEQ ID NO: 2, or a sequence complementary to the nucleotide sequence shown in SEQ ID NO: 1 or SEQ ID NO: 2. And, if primer extension product is obtained, it can be determined that the nucleic acid having the nucleotide sequence shown in SEQ ID NO: 1 or SEQ ID NO: 2, or a sequence complementary to the nucleotide sequence shown in SEQ ID NO: 1 or SEQ ID NO: 2 is present in the sample, namely it can be determined that *Chlamydia trachomatis* or its gene is present.

In addition, a sequence of further particular region in the nucleotide sequence shown in SEQ ID NO: 1 or SEQ ID NO: 2 or a sequence complementary to the nucleotide sequence shown in SEQ ID NO: 1 or SEQ ID NO: 2 may be set as a target. That is, for example, a sequence of further particular region in the nucleotide sequence shown in SEQ ID NO: 1 is set as a target, and a primer set which can amplify this sequence is designed. And, when a primer extension product is obtained by the PCR using said primer set, it can be determined that the nucleic acid having the nucleotide sequence of the target is present in the sample, namely, it can be determined that *Chlamydia trachomatis* or its gene is present.

In addition, the oligonucleotide of the present invention can also be used for designing primer or probe for detecting *Chlamydia trachomatis*. That is, on the basis of SEQ ID NO: 1 or the sequence complementary to the nucleotide sequence shown in SEQ ID NO: 1 : of the present invention, or SEQ ID NO: 2 or the sequence complementary to the nucleotide sequence shown in SEQ ID NO: 2, a primer or a probe may be designed according to a conventional procedure which will be described below.

The oligonucleotide capable of hybridizing with the endogenous plasmid gene of *Chlamydia trachomatis* of the present invention includes an oligonucleotide consisting of a nucleotide sequence capable of hybridizing with the endogenous plasmid gene of *Chlamydia trachomatis* under high stringent condition or stringent condition, and the like. The high stringent condition and the stringent condition are as described above.

It should be noted that the nucleotide sequence shown in SEQ ID NO: 3, SEQ ID NO: 4 and SEQ ID NO: 8 were designed on the basis of the nucleotide sequence shown in SEQ ID NO: 1.

The nucleotide sequence shown in SEQ ID NO: 5 to SEQ ID NO: 7, and SEQ ID NO: 9 were designed on the basis of the nucleotide sequence shown in SEQ ID NO: 2.

The oligonucleotide of the present invention may be either deoxyribonucleic acid (DNA) or ribonucleic acid (RNA). In the case of ribonucleic acid, it goes without saying that thymidine residue (T) may be read as uridine residue (U). In addition, it may be a DNA comprising uridine residue obtained by performing a synthesis with exchanging T of arbitral position to U. Also, it may be an RNA comprising thymidine residue exchanged U of arbitral position to T. In addition, there may be the oligonucleotide in which one or plural nucleotides are deleted, inserted or replaced. One or plural nucleotides may be modified nucleotide such as inosine (I).

The method for obtaining an oligonucleotide of the present invention includes, but not limited to, for example, the method for preparation by chemical synthesis well known per se, the method for obtaining an oligonucleotide or a polynucleotide by genetic engineering technique using a vector, and the like (cloning method). In the case where the oligonucleotides having about 15 to 30 nucleotides among oligonucleotides of the present invention are intended to be prepared, the chemical synthesis method has been employed commonly because it is possible to obtain an oligonucleotide of consistent quality without difficulty in larger scale at lower cost.

For example, the oligonucleotide is synthesized by the conventional phosphoramidite method using a DNA synthesizer performed usually for DNA synthesis, and the resultant is purified through anion exchange column chromatography, and thus, an objective oligonucleotide of the present invention can be obtained.

Alternatively, it may be purchased from subcontractors carry out synthesis of the oligonucleotide.

The primer of the present invention is used for detection of *Chlamydia trachomatis*, and which is "an oligonucleotide primer designed on the basis of the nucleotide sequence shown in SEQ ID NO: 1 or SEQ ID NO: 2, and being capable of hybridizing with the endogenous plasmid gene of *Chlamydia trachomatis*" (hereinafter, sometimes described as "a primer of the present invention").

That is, the primer of the present invention is designed on the basis of the nucleotide sequence of the region of nucleotide No. 4133 to nucleotide No. 4277 (consisting of a nucleotide sequence shown in SEQ ID NO: 1) or the region of nucleotide No. 32 to nucleotide No. 176 (consisting of a nucleotide sequence sown in SEQ ID NO: 2) of the endogenous plasmid (pLGV440) gene of *Chlamydia trachomatis* shown in SEQ ID NO:10. And, the above-described region or a further particular region in these regions can be amplified by performing the nucleic acid amplification reaction using these primers.

Moreover, the primer of the present invention can be used for amplifying a sequence complementary to the nucleotide sequence of the above-described region.

The method for designing primer on the basis of the nucleotide sequence shown in SEQ ID NO: 1 or SEQ ID NO: 2 includes, for example, the following method. That is, in consideration of the type of reaction [nucleic acid amplification reaction such as PCR (including real-time PCR), nucleic acid hybridization and the like] for which the relevant primer is used and reaction condition [for example, melting temperature (Tm value) and the like], the primer may be designed by selecting an appropriate length of an appropriate region from among a nucleotide sequence shown in SEQ ID NO: 1 or SEQ ID NO: 2 or a sequence complementary to the nucleotide sequence shown in SEQ ID NO: 1 or SEQ ID NO: 2.

In addition, the primer may be designed using a software commonly used for designing primer, for example, a web tool for a primer design, Primer 3 (Whitehead Institute for Biomedical Research) and the like.

In addition, the primer of the present invention is an oligonucleotide having a length of preferably 10 to 50 nucleotides, more preferably 10 to 35 nucleotides, further more preferably 18 to 25 nucleotides which is considered to be a number of nucleotide necessary for retaining specificity as a primer.

A specific example of "an oligonucleotide which is designed on the basis of the nucleotide sequence shown in SEQ ID NO: 1 or SEQ ID NO: 2 and being capable of hybridizing with the endogenous plasmid gene of *Chlamydia trachomatis*" (the oligonucleotide of the present invention) to be used for the primer of the present invention is the same as described in the above explanation for the oligonucleotide of the present invention. In addition, as to an oligonucleotide to be used for the primer of the present invention, there may exist deletion, insertion or replacement of one or plural nucleotides within the oligonucleotide depending on the condition, purpose etc. to be used.

Specific example of the primer of the present invention include, "an oligonucleotide primer comprising a nucleotide sequence shown in any one of SEQ ID NO: 3 to SEQ ID NO: 7, or a sequence complementary to the nucleotide sequence shown in any one of SEQ ID NO: 3 to SEQ ID NO: 7".

Also, the primer of the present invention comprises "a combination of forward primer and reverse primer selected from the oligonucleotide comprising a nucleotide sequence shown in any one of SEQ ID NO: 3 to SEQ ID NO: 7, or a complementary sequence to the nucleotide sequence shown in any one of SEQ ID NO: 3 to SEQ ID NO: 7".

In addition, preferable primer of the present invention, and their name denominated in the present invention are listed in Table 1 below.

TABLE 1

| SEQ ID NO | Name of Primers |
| --- | --- |
| SEQ ID NO: 3 | TcTI_Fw01 |
| SEQ ID NO: 4 | TcTI_Rv01 |
| SEQ ID NO: 5 | TcTI_Fw02m |
| SEQ ID NO: 6 | TcTI_Rv02 |
| SEQ ID NO: 7 | TcTI_Fw02 |

The method for obtaining the primer of the present invention is as described above in the method for obtaining the nucleotide of the present invention.

In addition, the primer of the present invention may be labeled with a labeling substance.

The method for labeling the primer of the present invention includes the labeling methods of the oligonucleotide to be usually conducted in this field, and the method may be selected appropriately depending on the each labeling substance.

As the labeling substance to be used for labeling the primer of the present invention, any kind of known labeling substances such as a radioisotope, an enzyme, a fluorescent substance, a luminescent substance, biotin can be used.

For example, the radioisotope such as $^{32}P$, $^{33}P$, $^{35}S$, the enzyme such as alkaline phosphatase, horseradish peroxidase, the fluorescent substance such as Alexa555, Alexa647 (manufactured by Invitrogen Corp.), Cy3, Cy5 of Cyanine dye series (manufactured by Amersham Biosciences K.K.), fluorescein, the luminescent substance such as chemoluminescent reagents including Acridinium Ester, and the like, are included.

The method for labeling the primer of the present invention with a radioisotope includes the method for labeling by incorporation of a radioisotope-labeled nucleotide into a primer at the time when the primer is synthesized, or the method for labeling with a radioisotope after the primer is synthesized, and the like. Specifically, random primer method which is commonly used frequently, nick-translation method, 5'-terminal labeling method using T4 polynucleotide kinase, 3'-terminal labeling method using terminal deoxynucleotidyl transferase, RNA labeling method and the like are included.

The method for labeling the primer of the present invention with enzyme includes direct labeling methods of conventional technique in this field, in which an enzyme molecule such as alkaline phosphatase, horseradish peroxidase and the like is directly and covalently linked to the primer to be labeled.

The method for labeling the primer of the present invention with fluorescent substance includes, for example, a method in which the fluorescent-labeled nucleotide is incorporated into the primer by a conventional labeling technique in this field. In addition, also, by a method of replacing a nucleotide in the oligonucleotide sequence with a nucleotide having a linker arm (see, for example, Nucleic Acids Res., 1986, vol. 14, p. 6115), the nucleotide can be labeled with fluorescent substance. In this case, there may be a method in which a uridine having a linker arm on 5-position is synthesized chemically from deoxyuridine by a synthesis method disclosed in JP-A-60-500717, and an oligonucleotide which comprises the deoxyuridine is synthesized, subsequently a fluorescent substance is introduced into the oligonucleotide chain (JP-A-60-50717).

The method for labeling the primer of the present invention with a luminescent substance or with biotin includes the conventional technique of luminescent-labeling or biotin-labeling which is usually performed for nucleotides in this field.

The probe of the present invention is used for detection of *Chlamydia trachomatis*, and that is "an oligonucleotide probe designed on the basis of the nucleotide sequence shown in SEQ ID NO: 1 or SEQ ID NO: 2 and being capable of hybridizing with the endogenous plasmid gene of *Chlamydia trachomatis*" (hereinafter, sometimes described as "the probe of the present invention").

In addition, the probe of the present invention includes the one which can hybridize with the nucleotide sequence of the region of nucleotide No. 4133 to nucleotide No. 4277 corresponding to SEQ ID NO: 1 or the region of nucleotide No. 32 to nucleotide No. 176 corresponding to SEQ ID NO: 2 of the endogenous plasmid gene of *Chlamydia trachomatis* shown in SEQ ID NO: 10, or the nucleotide sequence of a further particular region in these regions.

Further, the probe of the present invention comprises the one which can hybridize with a sequence complementary to the nucleotide sequence of the above-described region.

The probe of the present invention may be designed from a nucleotide sequence shown in SEQ ID NO:1 or SEQ ID NO:2 or a sequence complementary to the nucleotide sequence shown in SEQ ID NO:1 or SEQ ID NO:2, in compliance with the nucleic acid amplification reaction such as PCR (including real-time PCR) and the condition of nucleic acid hybridization and the like, and by selecting an appropriate length of an appropriate region in consideration of melting temperature (Tm value) and the like. When the probe is intended to retain sufficient specificity, it is desirable to design the probe in consideration of number of nucleotide necessary for retaining specificity as a probe sequence.

For example, as a probe to be used for the nucleic acid amplification method (for example, TaqMan™ method, Molecular Beacon method, and so on), it is desirable to have a length of 10 to 50 nucleotides, preferably 15 to 40 nucleotides, further preferably 20 to 30 nucleotides.

In addition, for example, as a probe to be used for the nucleic acid hybridization method (for example, Southern hybridization, and so on), and the like, it is desirable for the probe to have a length of 10 to 700 nucleotides, preferably 100 to 600 nucleotides, further preferably 100 to 500 nucleotides.

A specific example of "an oligonucleotide designed on the basis of the nucleotide sequence shown in SEQ ID NO: 1 or SEQ ID NO: 2 and being capable of hybridizing with the endogenous plasmid gene of *Chlamydia trachomatis*" (the oligonucleotide of the present invention) to be used for the probe of the present invention is the same as described in the above explanation for the oligonucleotide of the present invention.

Specific example of the probe of the present invention include, for example, an oligonucleotide probe comprising a nucleotide sequence shown in any one of SEQ ID NO: 1 to SEQ ID NO: 9, or a sequence complementary to the nucleotide sequence shown in any one of SEQ ID NO: 1 to SEQ ID NO: 9, which is designed on the basis of the nucleotide sequence shown in SEQ ID NO: 1 or SEQ ID NO: 2 by the above-described method.

A preferable probe includes an oligonucleotide probe which comprising a nucleotide sequence shown in SEQ ID NO: 8 or SEQ ID NO: 9, or a sequence complementary to the nucleotide sequence shown in SEQ ID NO: 8 or SEQ ID NO: 9.

The method for obtaining the probe of the present invention is as described above in the method for obtaining the nucleotide of the present invention.

Further, the probe of the present invention may be labeled with a labeling substance.

As the labeling substance to be used for labeling the probe of the present invention, any kind of known labeling substances such as radioisotope and enzyme, fluorescent substance, luminescent substance, biotin can be used.

Specific example of the labeling substance and the labeling method to be used for labeling the probe of the present invention include the same method as described in the labeling method of the primer of the present invention.

In addition, the labeled probe to be used in the detection method by the real-time detection method (for example, the real-time PCR such as TaqMan™ real-time PCR) as described later includes, for example, the probe of the present invention in which 5'-terminal was labeled with a reporter fluorescent substance and 3'-terminal was labeled with a quencher dye, as usually used in the real-time PCR method.

The reporter fluorescent substance for labeling the 5'-terminal of the probe of the present invention includes carboxyfluorescein (FAM™, trade name of Applera Corporation), hexachlorofluorescein (HEX), tetrachlorofluorescein (TET), Texas Red™ (trade name of Molecular Probe Inc.), Cy5, VIC, and so on.

The quencher dye for labeling the 3'-terminal of the probe of the present invention includes, for example, fluorescent substance such as carboxytetramethylrhodamine (TAMRA™, trade name of Applera Corporation), nonfluorescent substance such as Black Hole Quencher dye (BHQ™, trade name of Biosearch Technologies Inc., Novato, Calif.) and 4-((4-(dimethylamino) phenyl) azo) benzoic acid (DABCYL), and the like.

Specific labeled probe includes, for example, a labeled probe, in which an oligonucleotide comprising a nucleotide sequence shown in SEQ ID NO: 8 or SEQ ID NO: 9, or a complementary sequence to the nucleotide sequence shown in SEQ ID NO: 8 or SEQ ID NO: 9, is labeled with a reporter fluorescent substance and a quencher dye.

In the detection method by the TaqMan™ real-time PCR method to be described hereinafter, the above-described labeled probe can also be used.

The term "detection" in the detection method of *Chlamydia trachomatis* of the present invention encompasses a case where *Chlamydia trachomatis* in various kinds of clinical material such as patient specimen is intended to be detected or a case where species of isolated and cultured bacteria is intended to be determined, by amplifying and detecting a part of nucleotide sequence of the endogenous plasmid gene of *Chlamydia trachomatis*. In addition, use application of the detection method of the present invention includes, not limited to clinical field, but also the detection in the fundamental experiment in laboratory.

The specimen to be used for the detection of *Chlamydia trachomatis* of the present invention includes, for example, various kinds of clinical specimen such as urine, urethral swab suspension, cervical swab suspension, oral swab suspension. Before performing the detection process, these specimens may be subjected to, as a pretreatment in advance, an operation such as concentration and separation of the bacteria which may exist in the specimen, and isolation and concentration of nucleic acid from the bacterial cell. Such method includes the treatment by enzyme, surface active agent, alkaline and heat, etc.

Also, the sample used in the present invention includes, in addition to the above-described various kinds of clinical material, cultured bacterial cell and nucleic acid isolated and purified from these. In addition, it may be amplified nucleic acid.

Extraction and purification of DNA from the above-described samples may be performed according to the conventional procedure to be used for the extraction of chlamydia DNA from specimen.

For example, it may be performed by the following method.

First, the cell wall of chlamydia in the sample is needed to be broken down. The method for this purpose includes, for example, in the case where the bacterial cell is used as a sample, a method for disrupting the membrane structure of chlamydia by treating the bacterial cell with, for example, surface active agent such as SDS, or protein denaturing agent such as guanidine thiocyanate (GTC), and a method for disrupting physically the bacterial cell using glass beads and the like.

After disrupting the cell wall of the chlamydia, extraction and purification of DNA may be performed by a common method for preparation of DNA in this field [phenol-chloroform extraction, ethanol precipitation method, the method described in Rapid and simple method for purification of nucleic acids, J. Clin. Microbiol., 1990, March; 28 (3), 495-503, Boom R, Sol C J, Salimans M M, Jansen C L, Wertheim-van Dillen P M, van der Noordaa J, or the precipitation method using propanol, and the like].

For the extraction and purification of DNA, since various types of kits for this purpose are available in the market, such kits may be used. For example, the extraction and purification of the DNA may be performed using ion-exchange resin type DNA extraction and purification kit Genomic-tip (manufactured by Quiagen GmbH) and the like.

The detection method of *Chlamydia trachomatis* of the present invention is "A method for detecting *Chlamydia trachomatis*, comprising performing a nucleic acid amplification reaction using an oligonucleotide designed on the basis of the nucleotide sequence shown in SEQ ID NO: 1 or SEQ ID NO: 2 and being hybridizing with an endogenous plasmid gene of *Chlamydia trachomatis* (the oligonucleotide of the present invention) as a primer (the primer of the present invention), and using nucleic acid in a sample as a template, and detecting the resulting product obtained by the reaction.".

That is, the above-described method is the method in which by setting a region of nucleotide No. 4133 to nucleotide No. 4277 (SEQ ID NO: 1) or a region of nucleotide No. 32 to nucleotide No. 176 (SEQ ID NO: 2), or a further particular region within these regions of the endogenous plasmid gene of *Chlamydia trachomatis* shown in SEQ ID NO: 10, as a target, and by confirming whether the oligonucleotide having a nucleotide sequence of these region exists in a sample or not, *Chlamydia trachomatis* is detected.

Specific examples of the primer of the present invention to be used in the nucleic acid amplification reaction such as PCR include, for example, an oligonucleotide primer comprising a nucleotide sequence shown in any one of SEQ ID NO: 3 to SEQ ID NO: 7, or a sequence complementary to the nucleotide sequence shown in any one of SEQ ID NO: 3 to SEQ ID NO: 7.

In addition, preferable combination of primers (primer pair) to be used for the nucleic acid amplification reaction includes the followings:

(1) An oligonucleotide primer comprising a nucleotide sequence shown in SEQ ID NO: 3 or a complementary sequence thereof, and an oligonucleotide primer comprising a nucleotide sequence shown in SEQ ID NO: 4 or a complementary sequence thereof;

(2) An oligonucleotide primer comprising a nucleotide sequence shown in SEQ ID NO: 5 or a complementary sequence thereof, and an oligonucleotide primer comprising a nucleotide sequence shown in SEQ ID NO: 6 or a complementary sequence thereof; and (3) An oligonucleotide primer comprising a nucleotide sequence shown in SEQ ID NO: 7 or a complementary sequence thereof, and an oligonucleotide primer comprising a nucleotide sequence shown in SEQ ID NO: 6 or a complementary sequence thereof.

Other reagents such as deoxyribonucleoside triphosphate (dATP, dCTP, dGTP, dTTP), DNA polymerase to be used for the nucleic acid amplification reaction such as the real-time PCR using the above-described primers may use the same reagents as used commonly in this field, and except for the use of the primer and the probe of the present invention, the condition and the procedures etc. may be performed according to general protocol of the PCR method.

A specific example of the detection method of *Chlamydia trachomatis* of the present invention will be described below.

(A) A detection method of *Chlamydia trachomatis* in which, using the oligonucleotide of the present invention as a primer, the nucleic acid amplification reaction is performed with nucleic acid in a sample as a template, and then the resulting product obtained by the relevant reaction is detected.

In the method of (A), the method for performing the nucleic acid amplification reaction using the primer of the present invention includes, for example, a method in which the nucleic acid amplification reaction by DNA polymerase and the like, using the primer of the present invention and using nucleic acid in a sample as a template [for example, the polymerase chain reaction (PCR) method; LAMP (Loop-mediated Isothermal Amplification) method (Tsugunori Notomi et al., Nucleic Acid Res., 28, e63, 2000), ICANTM (Isothermal and Chimeric primer-initiated Amplification of Nucleic acids) method (Rinsho Byori (Clinical Pathology), 51(11), 1061-1067, 2003, November), LCR (ligase chain reaction) method (JP-A-4-211399), SDA (strand displacement amplification) method (JP-A-8-19394)]. And, by this method, the sequence of specific region of the endogenous plasmid gene of *Chlamydia trachomatis* can be amplified, and thus *Chlamydia trachomatis* can be detected by detecting and measuring the resulting primer extension product.

Among the methods for performing the above-described nucleic acid amplification reaction, the PCR method is included as the most common method.

In addition, as a method for performing the nucleic acid amplification reaction, for example, the real-time amplification detection method (see, for example, the description in U.S. Pat. Nos. 5,210,015 and 5,538,848) can be used. In addition, as an example of the detection method by the real-time amplification detection method, for example, the real-time PCR detection method is included.

An example of the real-time PCR detection method includes TaqMan™ real-time PCR method (see, for example, the description in U.S. Pat. No. 5,538,848), MGB Eclipse Probe System method (see, for example, the description in U.S. Pat. No. 5,801,155), Molecular Beacons Probe Technology method (see, for example, the description in U.S. Pat. No. 5,925,517), LUX Fluorogenic Primer method (Invitrogen Corp.) and Quenching probe-PCR (QP) method (see, for example, the description in U.S. Pat. No. 6,492,121), and the like.

The "method for detecting the resulting product of the nucleic acid amplification reaction" includes the conventional procedures commonly performed in this field, and is not particularly limited.

For example, in addition to the method quoted as an example of the above-described real-time PCR detection method and intercalator method, various detection method such as a method in which, after the nucleic acid amplification reaction is performed, the obtained primer extension products are subjected to electrophoresis, and the detection is performed on the basis of the obtained results from the electrophoresis, or a method in which the nucleic acid amplification reaction is performed using labeled primer, then the signal derived from the obtained primer extension product is measured, and so on are included.

Among them, the commonly used method includes, for example, the following methods:

(A-1) TaqMan™ real-time PCR method (TaqMan™ probe method);

(A-2) Intercalator method;

(A-3) A method in which, after the nucleic acid amplification reaction is performed, the obtained primer extension products are subjected to electrophoresis, and the detection is performed on the basis of the obtained results from the electrophoresis; and (A-4) A method in which, the nucleic acid amplification reaction is performed using a labeled primer, and then the signal derived from the obtained primer extension product is measured.

Each of these methods will be explained below.

(A-1) Taqman™ Real-Time PCR Method (Taqman™ Probe Method)

The TaqMan™ real-time PCR method is a method in which the real-time PCR is performed using a labeled probe which the 5'-terminal is labeled with a fluorescent dye (reporter), for example, such as FAM, and the 3'-terminal is labeled with a quencher dye, for example, such as TAMRA, and this fluorescent intensity is monitored in real time, and this is a method for detecting an objective very small amount of DNA with high sensitivity yet quantitatively.

In this method, initial amount of template DNA can be quantified accurately.

In addition, the TaqMan™ real-time PCR detection method generates a very little noise caused by nonspecific amplification reaction. Therefore, the method is a particularly excellent method in terms of the point that the amplification and detection of a target with higher specificity becomes possible.

As the primer to be used for the detection method of the present invention utilized the TaqMan™ real-time PCR method, the primer of the present invention is used. The preferable primer of the present invention includes the one which is used in the nucleic acid amplification reaction such as the above-described PCR method, and the preferable specific example and preferable combination of the primer are also as described above.

The probe to be used as a labeled probe of the present invention which the 5'-terminal is labeled with a fluorescent dye (reporter) and the 3'-terminal is labeled with a quencher dye and which is used for the TaqMan™ real-time PCR detection method, may be the above-described probe of the present invention. In a practical sense, a probe containing a nucleotide sequence of primer extension product which is anticipated to be obtained when the real-time PCR is performed using a selected primer in combination, or a probe containing a nucleotide sequence designed further from such sequence, may be used.

For example, when the detection method of the present invention is practiced by setting a region of nucleotide No. 4133 to nucleotide No. 4277 of the endogenous plasmid gene of *Chlamydia trachomatis* as a target, for example, the TaqMan™ real-time PCR is performed using a primer TcTI_Fw01 (SEQ ID NO: 3) and a primer TcTI_Rv01 (SEQ ID NO: 4) which are designed on the basis of the nucleotide sequence (shown in SEQ ID NO: 1) of the relevant region. In this case, a whole region of the relevant region is amplified. And so, in the case where the detection is performed using the primer TcTI_Fw01 (SEQ ID NO: 3) and the primer TcTI_Rv01 (SEQ ID NO: 4), an oligonucleotide designed on the basis of the nucleotide sequence (shown in SEQ ID NO: 1) of this region is used as a probe. For example, an oligonucleotide consisting of a sequence shown in SEQ ID NO: 8 (referred to as "TcTI_FwRv1") is included.

In addition, when the detection method of the present invention is practiced by setting a region of nucleotide No. 32 to nucleotide No. 176 of the endogenous plasmid at a target, for example, the TaqMan™ real-time PCR is performed using a primer TcTI_Fw02m (SEQ ID NO: 5) and a primer TcTI_Rv02 (SEQ ID NO: 6) which were designed on the basis of the nucleotide sequence (shown in SEQ ID NO: 2) of the relevant region. In this case, a region of nucleotide No. 63 to nucleotide No. 176 of the relevant region is amplified. And so, in the case where the detection is performed using the primer TcTI_Fw02m (SEQ ID NO: 5) and the primer TcTI_Rv02 (SEQ ID NO: 6), an oligonucleotide designed on the basis of the region of nucleotide No. 63 to nucleotide No. 176 is used as a probe. For example, an oligonucleotide consisting of a sequence shown in SEQ ID NO: 9 (referred to as "TcTI_FwRv2") is included.

In addition, the TaqMan™ real-time PCR is performed using another primer TcTI_Fw02 (SEQ ID NO: 7) and a primer TcTI_Rv02 (SEQ ID NO: 6) which were designed on the basis of the nucleotide sequence of a region of nucleotide No. 32 to nucleotide No. 176 of the endogenous plasmid gene. In this case, a whole region (nucleotide No. 32 to nucleotide No. 176) of the relevant region is amplified. And so, in the case where the detection is performed using the primer TcTI_Fw02 (SEQ ID NO: 7) and the primer TcTI_Rv02 (SEQ ID NO: 6), an oligonucleotide designed on the basis of the region of nucleotide No. 32 to nucleotide No. 176 is used as a probe. In this case also, for example, an oligonucleotide comprising a sequence shown in SEQ ID NO: 9 (referred to as "TcTI_FwRv2") can be used.

Other reagents to be used for the TaqMan™ real-time PCR detection method such as deoxyribonucleoside 3-phosphate (dATP, dCTP, dGTP, dTTP) and DNA polymerase may use the same reagents as usually used in the conventional real-time PCR, and the procedure of the TaqMan™ real-time PCR may be performing according to the customary protocol of the TaqMan™ real-time PCR except for the use of the primer and the probe of the present invention.

Taking "the method for detecting the resulting product of the nucleic acid amplification reaction" utilized the Taq-Man™ real-time PCR method as an example, the method would be explained as follows.

The PCR is performed using the primer of the present invention, and a labeled probe which is labeled with a reporter fluorescent dye on the 5'-terminal and with a quencher dye on the 3'-terminal of the probe of the present invention, and using the nucleic acid in a sample as a template, and then the fluorescence derived from reporter fluorescent dye released from said labeled probe is detected. As a result, when the fluorescence derived from reporter fluorescent dye is detected, it is determined that the sample is positive for *Chlamydia trachomatis* (namely, there exists *Chlamydia trachomatis*, or gene or gene segment (or fragment) thereof. The same shall apply hereinafter.).

In addition, in the TaqMan™ real-time PCR method, a calibration curve can be made, and therefore, the number of genomic DNA (copy number) of *Chlamydia trachomatis* in the sample can be obtained. In addition, since the number is proportional to the number of *Chlamydia trachomatis*, the number of *Chlamydia trachomatis* in a sample can also be determined.

The method for making up a calibration curve may be performed according to the routine procedure commonly performed in the real-time PCR method. For example, using genomic DNA sample of *Chlamydia trachomatis* with known copy number (diluted series) as a standard, the TaqMan™ real-time PCR is performed according to the above-described method, and the fluorescence intensity derived from the reporter dye is measured. On the basis of the obtained fluorescent intensity, amplification curve is made by the routine procedure. From the obtained amplification curve, threshold cycle (Ct) value is obtained by the routine procedure, then the Ct value (y-axis) is plotted for the logarithmic value (x-axis) of the copy number of DNA sample used for real-time PCR, and an approximated curve obtained for each Ct may be used as a calibration curve.

For quantitative determination of the number of genomic DNA (copy number) of *Chlamydia trachomatis* in the sample, the calibration curve obtained by the routine procedure as described above may be used.

That is, using genomic DNA sample of *Chlamydia trachomatis* with known copy number, the TaqMan™ real-time PCR is performed according to the above-described method, and the amplification curve is made by the same manner. The Ct value (threshold cycle value) in which the Threshold line (Th) at the time, when the calibration curve is made, crosses the obtained amplification curve, is obtained. By fitting its Ct value to the calibration curve, the quantity (copy number) of genomic DNA of *Chlamydia trachomatis* in the sample can be obtained.

A specific example of the TaqMan™ real-time PCR method used in the detection method of *Chlamydia trachomatis* of the present invention includes, for example, the following methods:

(1) The nucleic acid amplification reaction is performed using an oligonucleotide primer comprising a nucleotide sequence shown in SEQ ID NO: 3 or a complementary sequence thereof and an oligonucleotide primer comprising a nucleotide sequence shown in SEQ ID NO: 4 or a complementary sequence thereof, and using a labeled probe prepared by labeling the oligonucleotide comprising a nucleotide sequence shown in SEQ ID NO: 8 or a complementary sequence thereof with a reporter dye and a quencher dye, and using the nucleic acid in the sample as a template, and then the labeling substance released from the said labeled probe is detected, (2) The nucleic acid amplification reaction is performed using an oligonucleotide primer comprising a nucleotide sequence shown in SEQ ID NO: 5 or a complementary sequence thereof and an oligonucleotide primer comprising a nucleotide sequence shown in SEQ ID NO: 6 or a complementary sequence thereof, and using a labeled probe prepared by labeling the oligonucleotide comprising a nucleotide sequence shown in SEQ ID NO: 9 or a complementary sequence thereof with a reporter dye and a quencher dye, and using the nucleic acid in the sample as a template, and then the labeling substance released from the said labeled probe is detected, (3) The nucleic acid amplification reaction is performed using an oligonucleotide primer comprising a nucleotide sequence shown in SEQ ID NO: 7 or a complementary sequence thereof and an oligonucleotide primer comprising a nucleotide sequence shown in SEQ ID NO: 6 or a complementary sequence thereof, and using a labeled probe prepared by labeling the oligonucleotide comprising a nucleotide sequence shown in SEQ ID NO: 9 or a complementary sequence thereof with a reporter dye and a quencher dye, and using the nucleic acid in the sample as a template, and then the labeling substance released from the said labeled probe is detected.

As one example of the detection method of *Chlamydia trachomatis* by the TaqMan™ real-time PCR detection method of the present invention, taking a case where *Chlamydia trachomatis* is detected using the above-described "primer TcTI_Fw01" and the "primer TcTI_Rv01" of the present invention, as an example, the method would be explained as follows.

First, purified DNA sample is obtained from among a sample in which *Chlamydia trachomatis* should be detected by a known method.

Separately, for example, using a DNA synthesizer, an oligonucleotide consisting of a nucleotide sequence shown in SEQ ID NO: 3 (TcTI_Fw01) and an oligonucleotide consisting of a nucleotide sequence shown in SEQ ID NO: 4 (TcTI_Rv01) are synthesized by the phosphoramidite method.

In addition, from a nucleotide sequence which is anticipated to be amplified by the PCR using a primer pair of TcTI_Fw01 and TcTI_Rv01, a nucleotide sequence shown in SEQ ID NO: 8 (TcTI_FwRv1) is designed as sequence to be utilized as a probe, and an oligonucleotide having this nucleotide sequence is synthesized. The 5'-terminal of this oligonucleotide is coupled with a reporter dye FAM, and the 3'-terminal is coupled with a reporter quencher of TAMRA by routine procedure, and thus a fluorescence labeled probe is obtained.

Using the TcTI_Fw01 and TcTI_Rv01 synthesized in the above, as the primer for amplification, the real-time PCR is performed, for example, as follows.

That is, a 10 mM Tris-HCl buffer solution (pH 8.9) containing each 0.1 to 2 µM, preferably each 1 µM of the primer TcTI_Fw01 and primer TcTI_Rv01, 100 to 1000 nM fluorescence-labeled probe, 1.0 to 4.0 mM $MgCl_2$, KCl, BSA, sodium cholate, 0.005 to 0.2% TritonX-100, each about 0.2 mM of dATP, dCTP, dGTP and dTTP, and 10 to 80 unit/mL of Taq DNA polymerase is prepared, and is used as a reaction solution for PCR. To 20 µL of this reaction solution for PCR, 1 ng of the purified DNA sample is added to obtain a sample for PCR.

Using this sample for PCR, the real-time PCR is performed using real-time PCR detection equipment and the like. The reaction is repeated for 30 to 50 cycles, and at every cycle, the fluorescence intensity amount derived from the reporter dye is measured.

In this instance, when the fluorescence derived from reporter dye is measured, it may be determined that the sample is positive for *Chlamydia trachomatis*.

Further, by making a calibration curve according to the method described above, the number of *Chlamydia trachomatis* in the sample can be determined.

(A-2) Intercalator Method

By means of conventional intercalator method in which the real-time nucleic acid amplification reaction such as real-time PCR is performed using known intercalator, "detection of the resulting products of the nucleic acid amplification reaction" can be performed.

In the intercalator method, the electrophoresis after the nucleic acid amplification reaction is not necessary, and therefore, this is an effective method for a case where a rapid determination is required, in the field etc. of clinical test.

As the primer to be used for the detection method of the present invention utilizing the intercalator method, the primer of the present invention is used. Preferable primer of the present invention includes the one which is used in the above-described nucleic acid amplification reaction such as PCR method, and a preferable specific example and a preferable combination of the primers are as described above.

As the intercalator to be used in intercarlator method of the present invention, any type of intercalator usually used in this field, for example, SYBR™ Green I (trade name of Molecular Probes Inc.), ethidium bromide, fluorine and the like can be used.

An example of "the method for detecting the resulting products of the nucleic acid amplification reaction" utilized the intercalator method will be explained as follows.

Using the primer of the present invention and the intercalator (for example, SYBR™ Green I), and using as a sample a purified DNA sample isolated from a sample to be detected for *Chlamydia trachomatis*, the real-time PCR is performed using a polymerase such as Taq DNA polymerase. And, the fluorescence intensity derived from the intercalator, which intercalates with the primer extension products in correlation with the amplified amount, is measured.

Subsequently, by plotting the melting temperature of the primer extension product (double-stranded DNA) as horizontal axis and the first derivation (variation) of fluorescence intensity as vertical axis, melting curve is made. Using this, melting curve analysis of the primer extension product is performed, and thereby detection of peak is performed. Meanwhile, using a type strain of *Chlamydia trachomatis*, same measurement is performed to determine a peak. When a single peak is obtained for the sample, and Tm value (Tm peak value) of the peak is identical to the Tm peak value obtained using the type strain of *Chlamydia trachomatis*, it may be determined that the sample is positive for *Chlamydia trachomatis*.

In this regard, however, when the detection of *Chlamydia trachomatis* in a sample is performed using the same instrument, once the Tm peak value of the type strain has been confirmed, this Tm peak value may be used in the subsequent examination of samples, and a new confirmation of the Tm peak value of the type strain in each testing is not necessary In addition, on the basis of the measurement value obtained by the method utilized the intercalator method, a calibration curve can also be made according to the routine procedure usually performed in the real-time PCR, and therefore, using its calibration curve, the quantity (copy number) of genomic DNA of *Chlamydia trachomatis* in the sample can be obtained.

The method for making a calibration curve may be performed according to the routine procedure commonly performed in the real-time PCR method. For example, using genomic DNA sample of *Chlamydia trachomatis* with known copy number (diluted series) as a standard, the real-time PCR is performed according to the above-described method, the fluorescence intensity derived from intercalator is measured, and an amplification curve is made as well. From the obtained amplification curve, Ct value is determined by the routine procedure. And, the Ct value (y-axis) is plotted for the logarithmic value (x-axis) of the copy number of each DNA sample for PCR used in real-time PCR, and an approximated curve obtained for each Ct may be used as a calibration curve.

For the quantitative determination of the number (copy number) of genomic DNA of *Chlamydia trachomatis* in the sample, the calibration curve obtained by the routine procedure as described above may be used.

That is, after performing isolation and purification of DNA from the sample for detecting *Chlamydia trachomatis*, the real-time PCR by the intercalator method with respect to the obtained DNA sample is performed, and an amplification curve is made in the same manner, and the Ct value (threshold cycle value) at the point where the obtained amplification curve crosses the threshold line (Th) which was obtained when the calibration curve was made is obtained. By fitting its Ct value to the calibration curve, the quantity (copy number) of genomic DNA of *Chlamydia trachomatis* in the sample can be obtained.

Taking a case where *Chlamydia trachomatis* is detected using the above-described "primer TcTI_Fw01" and the "primer TcTI_Rv01" of the present invention as an example of the detection method of *Chlamydia trachomatis* by the real-time PCR detection method using intercalator relevant to the present invention, the method would be explained as follows.

First, by a known method, purified DNA sample is obtained from among a sample to be detected for *Chlamydia trachomatis*.

Separately, for example, using a DNA synthesizer, an oligonucleotide consisting of a nucleotide sequence shown in SEQ ID NO: 1 (TcTI_Fw01) and an oligonucleotide consisting of a nucleotide sequence shown in SEQ ID NO: 2 (TcTI_Rv01) are synthesized by the phosphoramidite method.

Using the synthesized TcTI_Fw01 and the TcTI_Rv01 as a primer for amplification, the real-time PCR is performed, for example, as follows.

That is, a 10 mM Tris-HCl buffer solution (pH 8.9) containing each 50 to 2000 nM of the primer TcTI_Fw01 and the primer TcTI_Rv01, about 5 to 100000 times dilution of the concentrate solution of intercalator [for example, SYBR™ Green I (product name of Molecular Probe Inc.)], 1.0 to 4.0 mM $MgCl_2$, KCl, BSA, sodium cholate, 0.005 to 0.2% TritonX-100, each about 0.2 mM of dATP, dCTP, dGTP and dTTP, and 10 to 80 U/mL of polymerase (for example, Taq DNA polymerase) is prepared, and is used as a reaction solution for PCR. To said reaction solution for PCR, the purified DNA sample purified from a sample to detect *Chlamydia trachomatis* is added, and is used as a sample for PCR. Using this sample for PCR, the real-time PCR is performed using real-time PCR detection equipment and the like. The reaction is repeated for 30 to 50 cycles, and at every cycle, the fluorescence intensity of the SYBR™ Green I which intercalates in correlation with the amplification quantity of the primer extension products is measured.

Subsequently, by plotting the melting temperature of the primer extension product (double-stranded DNA) as horizontal axis and the first derivation (variation) of fluorescence intensity as vertical axis, the melting curve is depicted. Using this, the melting curve analysis of the primer extension product is performed to detect the peak. When the obtained peak is a single peak, and it was confirmed that it appeared in the same position as the melting temperature of the peak obtained by measuring in the same way using a type strain of *Chlamydia trachomatis*, it may be determined that the sample is positive for *Chlamydia trachomatis*.

Further, by making a calibration curve according to the method described above, the number of *Chlamydia trachomatis* in the sample can be determined.

(A-3) A Method in which, after the Nucleic Acid Amplification Reaction is Performed, the Obtained Primer Extension Products are Subjected to Electrophoresis, and the Detection is Performed on the Basis of the Results of the Electrophoresis Specific example of the nucleic acid amplification reaction in said method is as described above. For example, the nucleic acid amplification method such as normal PCR method, and the real-time nucleic acid amplification method such as real-time PCR method are included.

The method for detecting *Chlamydia trachomatis* in which the electrophoresis is performed with respect to the primer extension product obtained by the nucleic acid amplification reaction and the detection is performed on the basis of the result of the electrophoresis includes, for example, (A-3-1) a method which is performed by confirming a fraction of primer extension product having objective size (number of base pair);

(A-3-2) a method which is detected by hybridization using labeled probe, and
(A-3-3) a method which detects the fluorescence derived from intercalator of the electrophoretic fraction.

Conditions, operation procedures and the like of the electrophoresis may be performed according to the conventional method usually performed in this field.

Each method will be described below.

(A-3-1) A Method which is Performed by Confirming a Fraction of Primer Extension Product Having Objective Size (Number of Base Pair)

For example, the electrophoresis is performed with respect to the primer extension product obtained by performing the nucleic acid amplification reaction.

Separately, from the combination of the primers used for the nucleic acid amplification reaction, size (number of base pair) of the primer extension product, which is anticipated to be amplified, is estimated in advance.

And, whether the obtained electrophoretic fraction is relevant to the estimated size of amplification product may be confirmed by the conventional method. For example, a method, in which the said fraction is stained by such a way that the nucleic acid species is visualized by staining with ethidium bromide and the like, and the size of the primer extension product is confirmed, and the like, is included. And when an oligonucleotide of a nucleotide sequence which is anticipated to be amplified by the combination of the used primers, or a fraction of a size of the number of its base pair is confirmed, it may be determined that "the sample is positive for *Chlamydia trachomatis*".

(A-3-2) A Method which is Detected by Hybridization Using Labeled Probe

For example, the electrophoresis is performed with respect to the primer extension product obtained by performing the nucleic acid amplification reaction.

Separately, the probe is designed based on the nucleotide sequence of primer extension product which is anticipated to be amplified from the combination of primers used for the nucleic acid amplification reaction, and a labeled probe is obtained by labeling the probe with labeling substance.

As for the obtained electrophoretic fraction, hybridization to the labeled probe is performed. And, when the presence of a fraction hybridized with said labeled probe is confirmed by detecting a signal derived from said labeled probe, it may be determined that "the sample is positive for *Chlamydia trachomatis*".

Specific examples of the probe and the labeling substance for labeling the probe to be used in said method, and the labeling method of the probe are as described above.

(A-3-3) A Method which Detects Fluorescence Derived from Intercalator of the Electrophoretic Fraction For example, the following methods are included.

(i) Using an oligonucleotide of the present invention as a primer, and using nucleic acid in the sample as a template, the nucleic acid amplification reaction by intercalator method is performed,
(ii) Primer extension product obtained in (i) is subjected to electrophoresis,
(iii) Conventional fluorescent detection is performed with respect to the electrophoretic fraction.

That is, if the primer extension product is obtained by the nucleic acid amplification reaction, the fluorescence derived from intercalator which has been incorporated into said primer extension product should be detected. And so, when an electrophoretic fraction which emits fluorescence derived from the intercalator is detected, it is determined that "the sample is positive for *Chlamydia trachomatis*".

In addition, in the nucleic acid amplification step, the present invention can apply a detection method utilized RNA transcription product. For example, it includes NASBA (nucleic acid sequence based amplification) method (JP-B-2650159), 3SR (self-sustained sequence replication) method (JP-B-7-114718), TAS (transcription based amplification system) method (JP-A-2-500565: WO 88/10315), TMA (transcription mediated amplification) method (JP-A-11-46778) and so on. Among them, the constant temperature nucleic acid amplification methods utilizing a concerted action (reaction is performed under such condition that the reverse transcriptase and the RNA polymerase are allowed to act concertedly) of reverse transcriptase and RNA polymerase is better suited for automation of the measurement system.

(A-4) A Method in which, after the Nucleic Acid Amplification Reaction is Performed Using a Labeled Primer, the Signal Derived from the Obtained Primer Extension Product is Measured The method of (A-4) includes a method in which, using a labeled primer labeled the primer of the present invention by the above-described method, and using nucleic acid in a sample as a template, the nucleic acid amplification reaction such as PCR is performed, and the signal derived from an obtained primer extension product is detected measured, and when the signal is detected, it is determined that the sample is positive for *Chlamydia trachomatis*.

In the case of above-described method, after the nucleic acid amplification reaction is performed, and prior to measurement of the signal derived from a primer extension product, an operation for removing free labeled primer by a known method may be performed. The method for removing the free labeled primer includes, for example, a method in which, after the primer extension product in the reactant obtained by performing the nucleic acid amplification reaction is precipitated by routine procedure for precipitating nucleic acid (ethanol precipitation method, a precipitation method using isopropanol and the like), the supernatant solution which contains non-precipitated free labeled primer is removed, and the like.

In addition, there are also included a method in which the reactant obtained by performing the nucleic acid amplification reaction is treated by gel chromatography under appropriate condition, thereby the primer extension product is separated from the free labeled primer, and a method for separating by electrophoresis method, and the like.

It should be noted that, in addition to the method described above, (B) there is also a method in which *Chlamydia trachomatis* is detected by using only the probe of the present invention. In this method, so called nucleic acid amplification reaction is not performed.

Specifically, for example, the following methods are included.

(B-1) It is a method that uses the one in which the probe of the present invention is bound to labeled a solid-phase carrier which was labeled with a labeling substance, or the one in which the labeled probe of the present invention which was labeled with a labeling substance (labeled probe) is bound to a solid-phase carrier as a capture probe. This capture probe is allowed to hybridize with the nucleic acid in the sample, and after immobilizing the nucleic acid derived from *Chlamydia trachomatis* in the sample on the solid-phase, the signal derived from the labeled probe or the signal derived from the labeled carrier is detected by routine procedure (see, for example, the description in JP-A-62-265999).

When the signal is detected, it may be determined that "the sample is positive for *Chlamydia trachomatis*".

(B-2) This is a method in which an unlabeled capture probe of (B-1) and a labeled probe which is the labeled probe of the present invention are used. These two probes are allowed to hybridize with a nucleic acid in the sample, and allowed to form a complex composed of the capture probe and a nucleic acid derived from *Chlamydia trachomatis* and the labeled probe on the solid phase carrier, and by performing a sandwich assay (see, for example, the description in JP-A-58-40099) for measuring the signal derived from the labeled probe, *Chlamydia trachomatis* is detected.

When the signal is detected, it is determined that "the sample is positive for *Chlamydia trachomatis*".

(B-3) This is a method in which, using a biotin-labeled probe of the present invention, the hybridization with a nucleic acid in the sample is performed, and after that, the nucleic acid derived from *Chlamydia trachomatis* in the sample is captured by an avidin-coupled carrier, and a complex of the nucleic acid derived from *Chlamydia trachomatis* and the avidin-coupled carrier is detected by a routine procedure.

When the complex is detected, it may be determined that "the sample is positive for *Chlamydia trachomatis*".

It should be noted that, as the reagents to be used for the detection method of *Chlamydia trachomatis* of the present invention, any reagent usually used in this field, for example, buffering agent, stabilizer, preservatives and the like can be used, so long as such reagents do not inhibit the stability of the coexisting reagents nor inhibit the nucleic acid amplification reaction such as PCR and hybridization reaction. In addition, the concentration may be selected as appropriate from the range of concentration usually used in this field.

Specific example of buffer solution includes all kinds of buffer solutions usually used for performing PCR and hybridization reaction, for example, such as Tris buffer solution, phosphate buffer solution, Veronal buffer solution, borate buffer solution and Good's buffer solution, and the pH of the buffer solution is not particularly limited, but generally a range between pH 5 to 9 is preferable.

In addition, as needed, nucleic acid synthetase (DNA polymerase, RNA polymerase, reverse transcriptase and the like), substrate (dNTP, rNTP and the like) according to enzyme, double strand intercalator (ethidium bromide, SYBR™ Green and the like), and substance for label detection such as FAM and TAMRA may be used.

A reagent kit for detection of *Chlamydia trachomatis* of the present invention includes "a reagent kit for detection of *Chlamydia trachomatis* comprising an oligonucleotide designed on the basis of the nucleotide sequence shown in SEQ ID NO: 1 or SEQ ID NO: 2 and being hybridizing with the endogenous plasmid gene of *Chlamydia trachomatis*, as a primer and/or a probe".

Specific examples of the primer of the present invention and the probe of the present invention which constitute the above-described kit are as described in the explanation for the above "the primer of the present invention" and "the probe of the present invention".

The primer and/or a probe of the present invention may be labeled with a labeling substance. Specific example of the labeling substance is as described above.

The kit comprising the primer of the present invention also encompasses a composition comprising a primer pair. A preferable combination of the primer pair is as follows.

(1) an oligonucleotide primer comprising a nucleotide sequence shown in SEQ ID NO: 3 or a complementary sequence thereof, and an oligonucleotide primer comprising a nucleotide sequence shown in SEQ ID NO: 4 or a complementary sequence thereof;

(2) an oligonucleotide primer comprising a nucleotide sequence shown in SEQ ID NO: 5 or a complementary sequence thereof, and an oligonucleotide primer comprising a nucleotide sequence shown in SEQ ID NO: 6 or a complementary sequence thereof; and (3) an oligonucleotide primer comprising a nucleotide sequence shown in SEQ ID NO: 7 or a complementary sequence thereof, and an oligonucleotide primer comprising a nucleotide sequence shown in SEQ ID NO: 6 or a complementary sequence thereof.

In addition, the above-described kit may further contain a labeled probe which labeled an oligonucleotide of the present invention with a labeling substance.

For example, the following compositions are included:

(1') an oligonucleotide primer comprising a nucleotide sequence shown in SEQ ID NO: 3 or a complementary sequence thereof, an oligonucleotide primer comprising a nucleotide sequence shown in SEQ ID NO: 4 or a complementary sequence thereof, and a labeled probe prepared by labeling an oligonucleotide comprising a nucleotide sequence shown in SEQ ID NO: 8 or a complementary sequence thereof with a labeling substance;

(2') an oligonucleotide primer comprising a nucleotide sequence shown in SEQ ID NO: 5 or a complementary sequence thereof, an oligonucleotide primer comprising a nucleotide sequence shown in SEQ ID NO: 6 or a complementary sequence thereof, and a labeled probe prepared by labeling an oligonucleotide comprising a nucleotide sequence shown in SEQ ID NO: 9 or a complementary sequence thereof with a labeling substance;

(3') an oligonucleotide primer comprising a nucleotide sequence shown in SEQ ID NO: 7 or a complementary sequence thereof, an oligonucleotide primer comprising a nucleotide sequence shown in SEQ ID NO: 6 or a complementary sequence thereof, and a labeled probe prepared by labeling an oligonucleotide comprising a nucleotide sequence shown in SEQ ID NO: 9 or a complementary sequence thereof with a labeling substance.

Preferable aspect and specific examples of constituent reagents which constitute these kits are as described above.

It should be noted that, the reagent kit for detection of *Chlamydia trachomatis* of the present invention may comprise, for example, buffering agent, stabilizer, preservatives and the like which neither inhibit the stability of the coexisting reagents and the like nor inhibit the nucleic acid amplification reaction such as PCR and the hybridization reaction. In addition, the concentrations may be selected as appropriate from the range of concentration usually used in this field.

Specific example of buffer solution includes all kinds of buffer solutions usually used for performing the PCR and the hybridization reaction, for example, such as Tris buffer solution, phosphate buffer solution, Veronal buffer solution, borate buffer solution, Good's buffer solution, and the pH is not particularly limited, but generally a range between pH 5 to 9 is preferable.

In addition, if necessary, the nucleic acid synthetase (DNA polymerase, RNA polymerase, reverse transcriptase and so on), the substrate (dNTP, rNTP, etc.) according to the enzyme, double strand intercalator (ethidium bromide, SYBR™ Green and the like), and substance for label detection such as FAM and TAMRA may be used.

Hereinafter, the present invention will be further explained in detail by referring to the following Examples, but the present invention should not be limited thereto at all.

EXAMPLES

All bacteria used in Examples are clinical isolates, and their bacterial species has already been differentiated by colony morphology and conventional various types of biochemical tests, after culturing.

Example 1

Targeting at a nucleotide sequence on the endogenous plasmid (pLGV440) gene of *Chlamydia trachomatis*, DNA amplification reaction was performed to evaluate specificity of the primer of the present invention.
(1) Determination of Target Sequence In the present invention, from a nucleotide sequence of the endogenous plasmid (pLGV440) gene of *Chlamydia trachomatis* (SEQ ID NO: 10), as a target sequence for detection of *Chlamydia trachomatis*, a nucleotide sequence with 145 by from 4133rd to 4277th and a nucleotide sequence with 145 by from 32nd to 176th were selected from within the nucleotide sequence shown in SEQ ID NO: 10. Each of the sequences was named as TcTI_Fw01Rv01 and TcTI_Fw02Rv02. The nucleotide sequence of TcTI_Fw01Rv01 was shown in SEQ ID NO: 1 of sequence listing and the nucleotide sequence of TcTI_Fw02Rv02 was shown in SEQ ID NO: 2 of sequence listing, respectively.
(2) Design and Synthesis of the Primer From the target sequence of TcTI_Fw01Rv01 specified in above (1), the primers for the PCR amplification detection, namely "5'-cgctcaaggaccagcaaata-3'" (hereinafter, referred to as "TcTI_Fw01". SEQ ID NO: 3) and "5'-gcttttccgcatc-caaac-3" (hereinafter, referred to as "TcTI_Rv01". SEQ ID NO: 4) were designed.

Synthesis of the oligonucleotide was commissioned to SIGMA-Genosys Corporation, and synthetic oligonucleotide having designed nucleotide sequence was obtained.
(3) Design and Synthesis of Labeled Probe From a nucleotide sequence which was anticipated to be amplified by the PCR using a combination of primers of TcTI_Fw01 and TcTI_Rv01 designed in above (2), a sequence to use as a probe was designed. Nucleotide sequence of the designed oligonucleotide was shown in SEQ ID NO: 8, and named as "TcTI_FwRv1".

Further, a labeled oligonucleotide probe, in which a reporter dye Texas Red™ was chemically bound to 5'-terminal of the "TcTI_FwRv1", and BHQ2™ of a reporter quencher was chemically bound to 3'-terminal thereof, was designed.

Synthesis and labeling of the oligonucleotide was contracted to SIGMA-Genosys Corporation, and the designed labeled probe was obtained.
(4) Preparation of DNA Sample Each chlamydia shown in the following Table 2 (genus *Chlamydia*: *Chlamydia trachomatis*, *Chlamydia pneumonia*, *Chlamydia psittaci*, *Chlamydia pecorum*; genus *Chlamydophila*: *Chlamydophila caviae*) was cultured according to the conventional procedures, and then the purified genomic DNA was obtained using known nucleic acids purification method. Each of the purified DNA obtained was adjusted to give final concentration of 1 ng/μL (in 10 mM Tris-HCl buffer, pH 8.9), and used as a DNA sample.

It should be noted that, all of the bacterial strains used were supplied by Professor Hiromi Kumon of School of Medicine, Okayama University.

TABLE 2

| species | strain |
|---|---|
| C. caviae | GPIC |
|  | OK135[Clinical Isolate] |
|  | OKM112[Clinical Isolate] |
|  | SC10[Clinical Isolate] |
| C. trachomatis | A (Serovar) |
|  | C (Serovar) |
|  | D (Serovar) |
|  | F (Serovar) |
|  | G (Serovar) |
|  | H (Serovar) |
|  | I (Serovar) |
|  | L1 (Serovar) |
|  | L2 (Serovar) |
|  | L3 (Serovar) |
| C. pneumoniae | TW183 |
|  | YK41 |
|  | KKpn15 |
|  | KKpn1 |
| C. psittaci | Cal10 |
|  | Budgerigan-1 |
|  | Izawa-1 |
| C. pecorum | Maeda |
|  | E58 |

(5) Real-Time PCR
1) Preparation of Reaction Solution for PCR

A 10 mM Tris-HCl buffer solution (pH 8.9) containing each 1 μM of primer TcTI_Fw01 and primer TcTI_Rv01 obtained in the above (2), 195 nM of labeled probe obtained in the above (3), 1.5 mM MgCl$_2$, 80 mM KCl, 500 μg/mL BSA, 0.1% sodium cholate, 0.1% Triton X-100, 0.2 mM each of dATP, dCTP, dGTP, and dTTP, and 40 unit/mL of Taq DNA polymerase (manufactured by Nippon Gene Co. Ltd.) was prepared and used as a reaction solution for PCR.
2) Real-Time PCR To 20 μL of the reaction solution for PCR, 1 μL of the DNA sample prepared in the above-described (4) was added and used as a sample for PCR. This was placed in a glass capillary tube for quantitative PCR reaction (manufactured by Roche A.G.), and the real-time PCR was performed using an exclusive thermal cycler•detector (LightCycler2.0; manufactured by Roche A.G.). As for reaction, after keeping the temperature at 95° C. for 10 minutes, a reaction cycle composed of heating at 95° C. for 15 seconds and at 60° C. for 1 minute was repeated for 50 cycles, and at every cycle, the fluorescence intensity derived from the reporter dye was measured. It should be noted that, the fluorescence intensity was obtained using a function for quantifying relative fluorescent intensity ratio, for every glass capillary tube provided to measurement of the thermal cycler used for measurement.
(6) Result The results of the obtained real-time PCR were summarized in the following Table 3. In Table 3, determination is "positive" indicates that the fluorescence signal was detected, on the other hand, determination is "negative" indicates that the fluorescence signal was not detected.

TABLE 3

| species | strain | Decision |
|---|---|---|
| C. caviae | GPIC | negative |
|  | OK135[Clinical Isolate] | negative |
|  | OKM112[Clinical Isolate] | negative |
|  | SC10[Clinical Isolate] | negative |

TABLE 3-continued

| species | strain | Decision |
|---|---|---|
| C. trachomatis | A (Serovar) | positive |
| | C (Serovar) | positive |
| | D (Serovar) | positive |
| | F (Serovar) | positive |
| | G (Serovar) | positive |
| | H (Serovar) | positive |
| | I (Serovar) | positive |
| | L1 (Serovar) | positive |
| | L2 (Serovar) | positive |
| | L3 (Serovar) | positive |
| C. pneumoniae | TW183 | negative |
| | YK41 | negative |
| | KKpn15 | negative |
| | KKpn1 | negative |
| C. psittaci | Cal10 | negative |
| | Budgerigan-1 | negative |
| | Izawa-1 | negative |
| C. pecorum | Maeda | negative |
| | E58 | negative |

As is clear from the result of Table 3, as a result of detection of the amplified nucleic acid by performing the real-time PCR using the combination of primer TcTI_Fw01 and primer TcTI_Rv01 of the present invention, and using the labeled probe of the present invention, the fluorescent signal generated as the result of nucleic acid amplification was confirmed only when the genomic DNA sample derived from every strain of Chlamydia trachomatis was used as a template. That is, these samples were determined as positive for Chlamydia trachomatis. On the other hand, when the real-time PCR was performed by the same way using the combination of the same primers, and using genomic DNA derived from bacterial cells other than Chlamydia trachomatis as a template, any corresponding fluorescent signal could not be detected. That is, all of these samples were determined as negative for Chlamydia trachomatis.

From the above, it turned out that, by performing the nucleic acid amplification reaction using the primer and the probe of the present invention, Chlamydia trachomatis could be detected specifically. In addition, the specificity of the primer and the probe of the present invention for Chlamydia trachomatis are high. Therefore, it can be expected the possibility that the nucleic acid obtained from clinical material can be applied as it is, without performing isolation of Chlamydia trachomatis, to the detection method using nucleic acid amplification reaction such as the PCR using the primer and the probe of the present invention.

Example 2

Using the real-time detection system, verification of detection sensitivity of the gene amplification system using primer sequence specified in the present invention was performed.

(1) Primer

TcTI_Fw01 and TcTI_Rv01 obtained in Example 1 (2) were used.

(2) Preparation of Labeled Probe

The labeled oligonucleotide probe, in which a reporter dye Texas Red™ was chemically bound to 5'-terminal of the "TcTI_FwRv1" and a reporter quencher BHQ2™ was chemically bound to 3'-terminal thereof, was used.

(3) Preparation of DNA Sample for PCR

After C. trachomatis [D (Serovar) strain] in Table 2 was cultured according to the conventional method, by the same method as used in Example 1 (4), purified genomic DNA was obtained using known nucleic acid purification procedure. This was dissolved in 10 mM Tris-HCl buffer to measure its absorbance. From the measurement value of absorbance, the quantity of genomic DNA (copy number of the genome) in the DNA sample was determined by calculating number of moles.

Subsequently, using 10 mM Tris-HCl buffer, pH 8.9, the one in which the DNA sample was diluted to a dilution series of $10^6$, $10^5$, $10^4$, $10^3$, $10^2$, 10, and 5 copy/μL was prepared and it was used as a DNA sample for PCR.

(4) Real-Time PCR

1) Preparation of Reaction Solution for PCR

A 10 mM Tris-HCl buffer solution (pH 8.9) containing each 1 μM of primer TcTI_Fw01 and primer TcTI_Rv01 obtained in the above (1), 195 nM of labeled probe obtained in the above (2), 1.5 mM $MgCl_2$, 80 mM KCl, 500 μg/mL BSA, 0.1% sodium cholate, 0.1% Triton X-100, 0.2 mM each of dATP, dCTP, dGTP, and dTTP, and 40 unit/mL of Taq DNA polymerase (manufactured by Nippon Gene Co. Ltd.) was prepared, and used as a reaction solution for PCR.

2) Real-Time PCR

The sequence TcTI_Fw01Rv01 was used as an amplification target in PCR, and the DNA sample for PCR (the dilution series) derived from C. trachomatis [D strain (Serovar)] prepared in the above-described (3) was used as a template DNA of the PCR.

First, to a 20 μL of the reaction solution for PCR, each 1 μL of the DNA sample for PCR prepared in the above-described (3) was added, and used as a sample for PCR. This was placed in a glass capillary tube for quantitative PCR reaction (manufactured by Roche Corporation), and the real-time PCR was performed using an exclusive thermal cycler•detector for the quantitative PCR (LightCycler2.0; manufactured by Roche Corporation). As for the reaction, after keeping the reaction temperature at 95° C. for 10 minutes, a reaction cycle composed of heating at 95° C. for 15 seconds and 60° C. for 1 minute was repeated for 50 cycles, and at every cycle, the fluorescence intensity derived from reporter dye was measured. It should be noted that, the fluorescence intensity was obtained using a function for quantifying relative fluorescent intensity ratio, for every glass capillary tube provided to measurement of the thermal cycler used for measurement.

(5) Result

From the obtained measurement result, a calibration curve was made according to the routine procedure commonly performed in the real-time PCR method.

That is, every DNA samples for PCR with each concentration, the fluorescence intensity (Rn, y-axis) derived from reporter dye was plotted for cycle number of PCR (x-axis) to make up an amplification curve. The obtained amplification curve was shown by FIG. 1.

Figure 1:
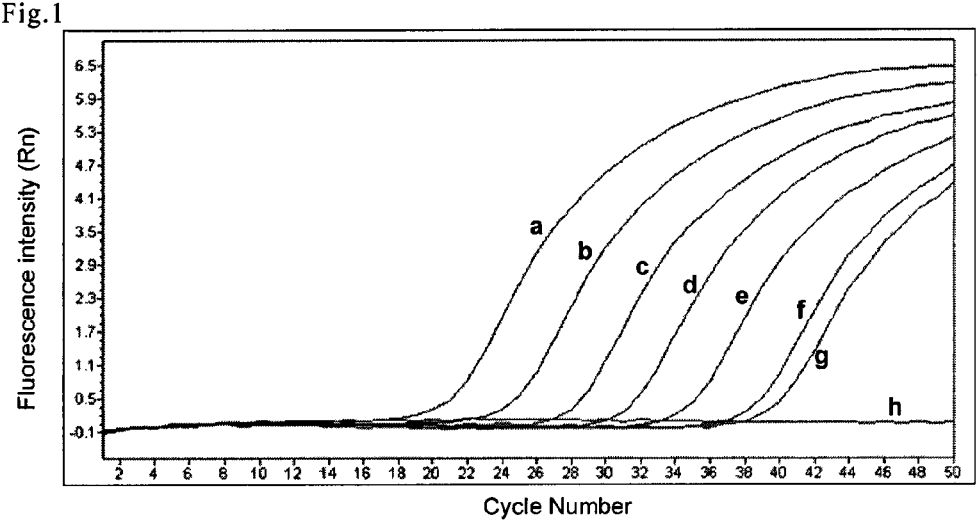
FIG. 1 shows an amplification curve obtained in Example 2, which is obtained by real time PCR using a primer TcTI_Fw01 and a primer TcTI_Rv01 and using a DNA sample derived from *Chlamydia trachomatis* as a template.

In FIG. 1, "a" to "h" in the figure represent the amplification curve in each case where the DNA sample for PCR of $10^6$, $10^5$, $10^4$, $10^3$, $10^2$, 10, and 5 copy/μL are used, respectively.

Subsequently, an Rn part where the fluorescence intensity is amplifying exponentially was selected, and a Threshold line (Th) was drawn. The crossing point of the Th with the fluorescence intensity of each DNA sample for PCR was defined as Threshold cycle (Ct). Subsequently, the Ct value (y-axis) was plotted for the copy number (x-axis) of the genome of each DNA sample for PCR used, and the approximated curve obtained for each Ct was used as a calibration curve. The obtained calibration curve was shown in FIG. 2.

From the result of FIG. 2, it turned out that, as detection sensitivity, the amplification detection up to 5 copy/reaction is possible. In addition, PCR efficiency was 1.979 (95.3%).

From the results above, it turned out that by performing the real-time PCR using an oligonucleotide relevant to the present invention as a primer, *Chlamydia trachomatis* can be detected in high sensitivity.

In addition, it also turned out that, since the calibration curve could be made, quantitative determination of *Chlamydia trachomatis* is possible by performing the real-time PCR using the primer and the probe of the present invention. Further, it turned out that the real-time PCR method using the primer and the probe of the present invention can detect *Chlamydia trachomatis* even under the condition where 5 copies of the genomic DNA of *Chlamydia trachomatis* are present as initial amount, and therefore, the detection of *Chlamydia trachomatis* can be performed in high detection sensitivity.

Furthermore, in the case where the real-time PCR method is utilized, quantitative determination of the initial amount of template DNA can be performed accurately, because this fluorescence intensity is monitored in real time, and therefore, the method is effective for the determination of *Chlamydia trachomatis*.

Example 3

Using the real-time detection system, verification of detection sensitivity of the gene amplification system using primer sequence specified in the present invention was performed.
(1) Design and Synthesis of the Primer
From the sequence (SEQ ID NO: 2) of the target sequence TcTI_Fw02Rv02 which was specified in Example 1 (1), the primers for the PCR amplification detection, namely "5'-cagatttcctttcgcattaaaaa-3'" (hereinafter, referred to as "TcTI_Fw02m"; SEQ ID NO: 5) and "5'-tctcccatttctccca-caag-3'" (hereinafter, referred to as "TcTI_Rv02"; SEQ ID NO: 6) were designed.

Synthesis of the oligonucleotide was commissioned to SIGMA-Genosys Corporation, and synthetic oligonucleotide having designed nucleotide sequence was obtained. These oligonucleotides were used as primer.
(2) Design and Synthesis of Labeled Probe
From a nucleotide sequence which is anticipated to be amplified by the PCR using the combination of primers of TcTI_Fw02m and TcTI_Rv02 designed in the above-described (1), a sequence to be used as a probe was designed. Nucleotide sequence of the designed oligonucleotide was shown in SEQ ID NO: 9, and was named as "TcTI_FwRv2".

Further, a labeled oligonucleotide probe in which a reporter dye Texas Red™ was chemically bound to 5'-terminal of the "TcTI_FwRv2", and a reporter quencher BHQ2™ was chemically bound to 3'-terminal thereof was designed.

Synthesis and labeling of the oligonucleotide was commissioned to by SIGMA-Genosys Corporation, and designed labeled probe was obtained.
(3) Preparation of DNA Sample for PCR
After *C. trachomatis* [D strain (Serovar)] in Table 2 was cultured according to the conventional method, by the same method as used in Example 1 (4), purified genomic DNA was obtained using known nucleic acid purification procedure. This was dissolved in 10 mM Tris-HCl buffer to measure its absorbance. From the measurement value of absorbance obtained, the quantity (copy number of the genome) of genomic DNA in the DNA sample was determined by calculating number of moles.

Subsequently, using 10 mM Tris-HCl buffer, pH 8.9, the one in which the DNA sample was diluted to a dilution series of $10^6$, $10^5$, $10^4$, $10^3$, $10^2$, 10, and 5 copy/μL was prepared and it was used as a DNA sample for PCR.

(4) Real-Time PCR
1) Preparation of Reaction Solution for PCR
A 10 mM Tris-HCl buffer solution (pH 8.9) containing each 1 μM of primer TcTI_Fw02m and primer TcTI_Rv02 obtained in the above (1), 195 nM of labeled probe obtained in the above (3), 1.5 mM $MgCl_2$, 80 mM KCl, 500 μg/mL BSA, 0.1% sodium cholate, 0.1% Triton X-100, 0.2 mM each of dATP, dCTP, dGTP, and dTTP, and 40 unit/mL of Taq DNA polymerase (manufactured by Nippon Gene Co. Ltd.) was prepared, and used as a reaction solution for PCR.
2) Real-Time PCR
The sequence TcTI_Fw02Rv02 was used as an amplification target in the PCR, and the DNA sample for PCR (the dilution series) derived from *C. trachomatis* [D strain (Serovar)] prepared in the above-described (3) was used as a template of the PCR.

First, to a 20 μL of the reaction solution for PCR, 1 μL of each DNA sample for PCR prepared in the above-described (3) was added, and used as a sample for PCR. This sample for PCR was placed in each well of a 96-well reaction plate (MicroAmp Optical 96-well Reaction Plate, manufactured by Applied Biosystems Japan Ltd.), and the PCR was performed using a real-time PCR detector (ABI 7500, manufactured by Applied Biosystems Japan Ltd.). As for the reaction, after keeping the reaction temperature at 95° C. for 10 minutes, a reaction cycle composed of heating at 95° C. for 15 seconds and 60° C. for 1 minute was repeated for 50 cycles, and at every cycle, the fluorescence intensity derived from reporter dye was measured. It should be noted that, the fluorescence intensity was determined for each sample well by using a function of quantifying relative fluorescent intensity ratio provided to the thermal cycler used for the measurement.
(5) Result
From the measurement result obtained, a calibration curve was made according to the routine procedure commonly performed in the real-time PCR method.

That is, every DNA samples for PCR with each concentration, the fluorescence intensity (Rn, y-axis) derived from reporter dye was plotted for each cycle number (x-axis) of PCR to make up an amplification curve. The obtained amplification curve was shown in FIG. 3.

Figure 3:
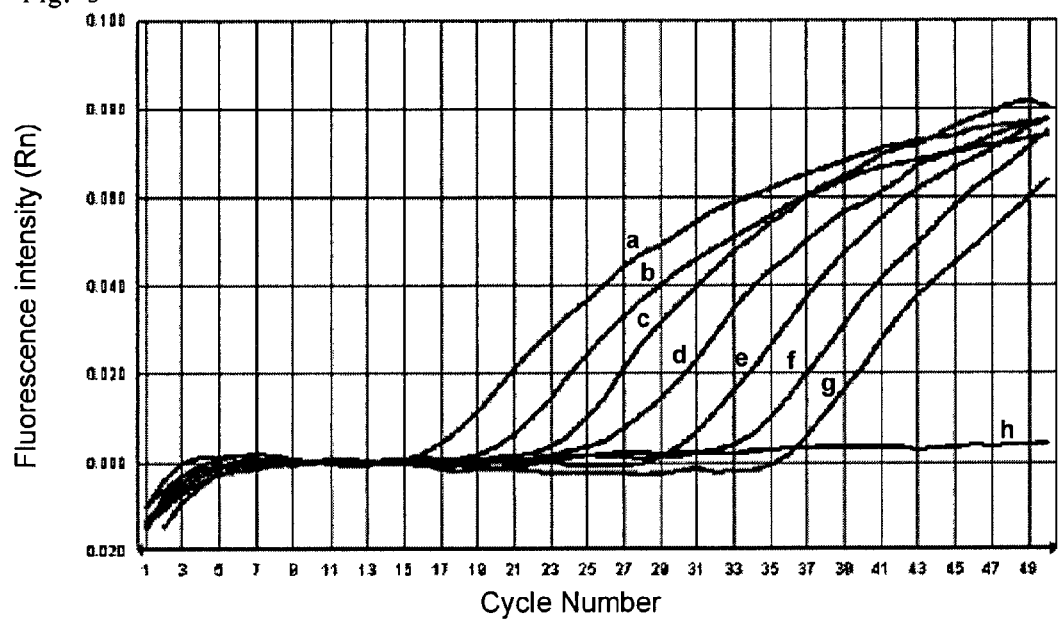
FIG. 3 shows amplification curve obtained in Example 3, which is obtained by the real time PCR using a primer TcTI_Fw02m and a primer TcTI_Rv02 and using a DNA sample derived from *Chlamydia trachomatis* as a template.

In FIG. 3, "a" to "h" in the figure represent the amplification curve in each case where the DNA sample for PCR of $10^6$, $10^5$, $10^4$, $10^3$, $10^2$, 10, and 5 copy/μL are used, respectively.

Subsequently, an Rn part where the fluorescence intensity is amplifying exponentially was selected, and a Threshold line (Th) was drawn. The crossing point of the Th with the fluorescence intensity of each DNA sample for PCR was defined as Threshold cycle (Ct). Subsequently, the Ct value (y-axis) was plotted for the copy number (x-axis) of the genome of each used DNA sample for PCR, and the approximated curve obtained for each Ct was used as a calibration curve. The calibration curve obtained was shown in FIG. 4.

Regression line formula obtained by regression analysis of the obtained calibration curve and correlation coefficient were as follows:

$$y=-3.421358x+40.971924$$

$$R^2=0.922401$$

Figure 4:
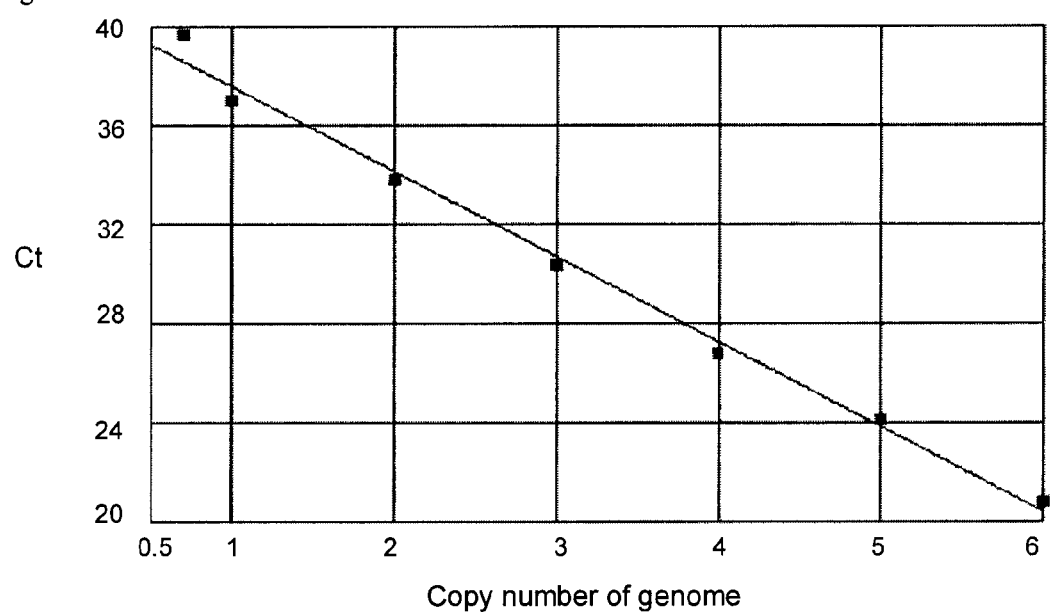
FIG. 4 shows a calibration curve made up on the basis of the amplification curve obtained by the real time PCR performed in Example 3, by plotting Ct value (y-axis) for the copy number of genome (x-axis, logarithmic scale).

As is clear from FIG. 4, a good (good linearity) calibration curve was obtained. In consequence, it turns out that quantification of *Chlamydia trachomatis* can be achieved by performing the nucleic acid amplification reaction using the primer and the probe of the present invention.

In addition, from the results shown in FIG. 4, it turns out that, as a detection sensitivity limit, the amplification detection is achieved up to 5 copies/reaction. That is, if the detection method using the primer and the probe of the present invention is performed, *Chlamydia trachomatis* can be detected even under the condition where only 5 copies of the genomic DNA of *Chlamydia trachomatis* are present as initial amount.

In addition, amplification efficiency of the practiced PCR (PCR Efficiency) was 96.1%, and was close to about 100%.

From the results described above, it turns out that, using the TcTI_Fw02Rv02 as an amplification target of the PCR, when the real-time PCR is performed using the combination of primer TcTI_Fw02m and primer TcTI_Rv02 and using the labeled probe of the present invention, *Chlamydia trachomatis* can be detected with high sensitivity and specificity to the same efficiency as the case where, using the TcTI_Fw01Rv01 as an amplification target of the PCR, the real-time PCR was performed using the combination of primer TcTI_Fw01 and primer TcTI_Rv01, and the labeled probe of the present invention.

Furthermore, in the case where the real-time PCR method is utilized, quantitative determination of the initial amount of template DNA can be performed accurately, because the fluorescence intensity is monitored in real time, and in this respect, the method is effective for the determination of *Chlamydia trachomatis*.

INDUSTRIAL APPLICABILITY

According to the detection method of *Chlamydia trachomatis* using the primer and/or the probe of the present invention, the detection of *Chlamydia trachomatis* can be performed more rapidly and with high precision as compared with a conventional method for identifying bacterial species by culture examination etc. of bacteria. In addition, the detection of *Chlamydia trachomatis* by detection method of the present invention can exclude any false-negative judgment in the diagnosis and can also detect and diagnose *Chlamydia trachomatis* with high precision. Further, it is accomplished an effect that quantification of the *Chlamydia trachomatis* itself can be performed by using the detection method of the present invention.

DESCRIPTION OF SYMBOLS

In FIG. 1, each symbol represents the following cases:
a: The case where the real-time PCR is performed targeting at TcTI_Fw01Rv01, using $10^6$ copies of initial DNA concentration in DNA sample for PCR;
b: The case where the real-time PCR is performed targeting at TcTI_Fw01Rv01, using $10^5$ copies of initial DNA concentration in DNA sample for PCR;
c: The case where the real-time PCR is performed targeting at TcTI_Fw01Rv01, using $10^4$ copies of initial DNA concentration in DNA sample for PCR;
d: The case where the real-time PCR is performed targeting at TcTI_Fw01Rv01, using $10^3$ copies of initial DNA concentration in DNA sample for PCR;
e: The case where the real-time PCR is performed targeting at TcTI_Fw01Rv01, using $10^2$ copies of initial DNA concentration in DNA sample for PCR;
f: The case where the real-time PCR is performed targeting at TcTI_Fw01Rv01, using 10 copies of initial DNA concentration in DNA sample for PCR;
g: The case where the real-time PCR is performed targeting at TcTI_Fw01Rv01, using 5 copies of initial DNA concentration in DNA sample for PCR;
h: The case where the real-time PCR is performed targeting at TcTI_Fw01Rv01, using 0 copy of initial DNA concentration in DNA sample for PCR.

In FIG. 3, each symbol represents the following cases:
a: The case where the real-time PCR is performed targeting at TcTI_Fw02Rv02, using $10^6$ copies of initial DNA concentration in DNA sample for PCR;
b: The case where the real-time PCR is performed targeting at TcTI_Fw02Rv02, using $10^5$ copies of initial DNA concentration in DNA sample for PCR;
c: The case where the real-time PCR is performed targeting at TcTI_Fw02Rv02, using $10^4$ copies of initial DNA concentration in DNA sample for PCR;
d: The case where the real-time PCR is performed targeting at TcTI_Fw02Rv02, using $10^3$ copies of initial DNA concentration in DNA sample for PCR;
e: The case where the real-time PCR is performed targeting at TcTI_Fw02Rv02, using $10^2$ copies of initial DNA concentration in DNA sample for PCR;
f: The case where the real-time PCR is performed targeting at TcTI_Fw02Rv02, using 10 copies of initial DNA concentration in DNA sample for PCR;
g: The case where the real-time PCR is performed targeting at TcTI_Fw02Rv02, using 5 copies of initial DNA concentration in DNA sample for PCR;
h: The case where the real-time PCR is performed targeting at TcTI_Fw02Rv02, using 0 copy of initial DNA concentration in DNA sample for PCR.

What is claimed is:

1. A method for detecting the presence or absence of *Chlamydia trachomatis* in a sample, the method comprising:
    obtaining a sample from a human subject; mixing the sample with a first oligonucleotide primer consisting of the nucleotide sequence of SEQ ID NO: 3, and a second oligonucleotide primer consisting of the nucleotide sequence of SEQ ID NO: 4 in a solution;
    subjecting the solution to a nucleic acid amplification reaction; and
    detecting the presence of *Chlamydia trachomatis* in the sample by detecting an amplification product or detecting the absence of *Chlamydia trachomatis* in the sample by detecting the absence of an amplification product.

2. The method according to claim 1, wherein the nucleic acid amplification reaction is real-time PCR.

3. The method according to claim 1, wherein the detecting comprises using an intercalator.

4. A method for detecting the presence or absence of *Chlamydia trachomatis* in a sample, the method comprising:
    obtaining a sample from a human subject;
    mixing the sample with a first oligonucleotide primer consisting of the nucleotide sequence of SEQ ID NO: 3, a second oligonucleotide primer consisting of the nucleotide sequence of SEQ ID NO: 4, and an oligonucleotide probe labeled with a reporter dye and a quencher fluorescent dye, in a solution;
    subjecting the solution to a nucleic acid amplification reaction, wherein the oligonucleotide probe is capable of hybridizing to a region of an amplification product produced by the amplification reaction; and
    detecting the presence of *Chlamydia trachomatis* in the sample by detecting an amplification product or detecting the absence of *Chlamydia trachomatis* in the sample by detecting the absence of an amplification product.

5. The method according to claim 4, wherein the labeled oligonucleotide probe comprises the nucleotide sequence of SEQ ID NO: 8 or the complementary sequence thereof; and wherein the detecting comprises detecting the reporter dye derived from the labeled oligonucleotide probe.

6. The method according to claim 1, wherein the detecting comprises detecting the presence or absence of an amplification product by performing electrophoresis on the solution following the nucleic acid amplification reaction.

7. The method according to claim 4, wherein the nucleotide sequence of the oligonucleotide probe consists of 10 to 50 contiguous nucleotides of the nucleotide sequence of SEQ ID NO: 1 or the complementary sequence thereof.

* * * * *

UNITED STATES PATENT AND TRADEMARK OFFICE
CERTIFICATE OF CORRECTION

PATENT NO.        : 9,458,513 B2
APPLICATION NO.   : 13/636250
DATED             : October 4, 2016
INVENTOR(S)       : Tomokazu Ishikawa et al.

It is certified that error appears in the above-identified patent and that said Letters Patent is hereby corrected as shown below:

In the Claims

Claim 1, Column 39, Line 40, "SEQ ID NO: 4in a solution" should read -- SEQ ID NO: 4, in a solution --.

Signed and Sealed this
Tenth Day of January, 2017

Michelle K. Lee
*Director of the United States Patent and Trademark Office*

SEQUENCE LISTING

```
<160> NUMBER OF SEQ ID NOS: 10

<210> SEQ ID NO 1
<211> LENGTH: 145
<212> TYPE: DNA
<213> ORGANISM: Chlamydia trachomatis

<400> SEQUENCE: 1
cgctcaagga ccagcaaata atccttggga caacatcaac acctgtcgca gccaaaatga      60
cagcttctga tggaatatct ttaacagtct ccaataatcc atcaaccaat gcttctatta    120
caattggttt ggatgcggaa aaagc                                          145

<210> SEQ ID NO 2
<211> LENGTH: 145
<212> TYPE: DNA
```

<213> ORGANISM: Chlamydia trachomatis

<400> SEQUENCE: 2

| gcgcacagac gatctatttt ttgcatccaa tcagatttcc tttcgcatta aaaaaagaca | 60 |
| gaataaagaa accaaaattc taatcacatt tcctatcagc ttaatggagg agttgcaaaa | 120 |
| atacacttgt gggagaaatg ggaga | 145 |

<210> SEQ ID NO 3  
<211> LENGTH: 20  
<212> TYPE: DNA  
<213> ORGANISM: Artificial  
<220> FEATURE:  
<223> OTHER INFORMATION: oligonucleotide primer

<400> SEQUENCE: 3

| cgctcaagga ccagcaaata | 20 |

<210> SEQ ID NO 4  
<211> LENGTH: 19  
<212> TYPE: DNA  
<213> ORGANISM: Artificial  
<220> FEATURE:  
<223> OTHER INFORMATION: oligonucleotide primer

<400> SEQUENCE: 4

| gcttttccg catccaaac | 19 |

<210> SEQ ID NO 5  
<211> LENGTH: 23  
<212> TYPE: DNA  
<213> ORGANISM: Artificial  
<220> FEATURE:  
<223> OTHER INFORMATION: oligonucleotide primer

<400> SEQUENCE: 5

| cagatttcct ttcgcattaa aaa | 23 |

<210> SEQ ID NO 6  
<211> LENGTH: 20  
<212> TYPE: DNA  
<213> ORGANISM: Artificial  
<220> FEATURE:  
<223> OTHER INFORMATION: oligonucleotide primer

<400> SEQUENCE: 6

| tctcccattt ctcccacaag | 20 |

<210> SEQ ID NO 7  
<211> LENGTH: 21  
<212> TYPE: DNA  
<213> ORGANISM: Artificial  
<220> FEATURE:  
<223> OTHER INFORMATION: oligonucleotide primer

<400> SEQUENCE: 7

| gcgcacagac gatctatttt t | 21 |

<210> SEQ ID NO 8  
<211> LENGTH: 23  
<212> TYPE: DNA  
<213> ORGANISM: Artificial  
<220> FEATURE:  
<223> OTHER INFORMATION: oligonucleotide probe

<400> SEQUENCE: 8
caacacctgt cgcagccaaa atg                                                23

<210> SEQ ID NO 9
<211> LENGTH: 29
<212> TYPE: DNA
<213> ORGANISM: Artificial
<220> FEATURE:
<223> OTHER INFORMATION: oligonucleotide probe

<400> SEQUENCE: 9
tcctatcagc ttaatggagg agttgcaaa                                          29

<210> SEQ ID NO 10
<211> LENGTH: 7498
<212> TYPE: DNA
<213> ORGANISM: Chlamydia trachomatis

<400> SEQUENCE: 10
ggatccgtaa gttagacgaa attttgtctt tgcgcacaga cgatctattt tttgcatcca        60
atcagatttc ctttcgcatt aaaaaaagac agaataaaga aaccaaaatt ctaatcacat       120
ttcctatcag cttaatggag gagttgcaaa atacacttg tgggagaaat gggagagtat       180
ttgtttctaa ataggggatt cctgtaacaa caagtcaggt tgcgcataat tttaggcttg       240
cagagttcta tagtgctatg aaaataaaaa ttactcctag agtacttcgt gcaagcgctt       300
tgattcattt aaagcaaata ggattaaaag atgaggaaat catgcgtatt tcctgtcttt       360
catcgagaca aagtgtgtgt tcttattgtt ctggggaaga ggtaagtcct ctagtacaaa       420
caccccaat attgtgatat aattaaaatt atattcatat tctgttgcca gaaaaaacac       480
ttttaggcta tattagagcc tcttctttga agcgttgtct tctcgagaag atttatcgta       540
cgcaaatatc atctttgcgg ttgcgtgtcc tgtgaccttc attatgtcgg agtctgagca       600
ccctaggcgt ttgtactccg tcacagcggt tgctcgaagc acgtgcgggg ttatcttaaa       660
agggattgca gcttgtagtc ctgcttgaga gaacgtgcgg gcgatttgcc ttaaccccac       720
cattttccg gagcgagtta cgaagacaaa acctcttcgt tgaccgatgt actcttgtag       780
aaagtgcata aacttctgag gataagttat aataatcctc ttttctgtct gacggttctt       840
aagctgggag aaagaaatgg tagcttgttg gaaacaaatc tgactaatct ccaagcttaa       900
gacttcagag gagcgtttac ctccttggag cattgtctgg gcgatcaacc aatcccgggc       960
attgattttt tttagctctt ttaggaagga cgctgtttgc aaactgttca tcgcatctgt      1020
ttttactatt tccctggttt taaaaaatgt tcgactattt tcttgtttag aaggttgcgc      1080
tatagcgact attccttgag tcatcctgtt taggaatctt gttaaggaaa tatagcttgc      1140
tgctcgaact tgtttagtac ttcggtccaa gaagtcttgg cagaggaaac ttttttaatc      1200
gcatctagaa ttagattatg atttaaaagg gaaaactctt gcagattcat atccaaggac      1260
aatagaccaa tcttttctaa agacaaaaaa gatcctcgat atgatctaca agtatgtttg      1320
ttgagtgatg cggtccaatg cataataact tcgaataagg agaagctttt catgcgtttc      1380
caataggatt cttggcgaat ttttaaaact tcctgataag acttttcgct atattctaac      1440
gacatttctt gctgcaaaga taaatccct ttacccatga aatccctcgt gatataacct      1500
atccgtaaaa tgtcctgatt agtgaaataa tcaggttgtt aacaggatag cacgctcggt      1560
attttttat ataaacatga aaactcgttc cgaaatagaa aatcgcatgc aagatatcga      1620
gtatgcgttg ttaggtaaag ctctgatatt tgaagactct actgagtata ttctgaggca      1680

```
gcttgctaat tatgagttta agtgttctca tcataaaaac atattcatag tatttaaata    1740
cttaaaagac aatggattac ctataactgt agactcggct tgggaagagc ttttgcggcg    1800
tcgtatcaag atatggacaa atcgtatctc gggttaatgt tgcatgatgc tttatcaaat    1860
gacaagctta gatccgtttc tcatacggtt ttcctcgatg atttgagcgt gtgtagcgct    1920
gaagaaaatt tgagtaattt cattttccgc tcgtttaatg agtacaatga aaatccattg    1980
cgtagatctc cgtttctatt gcttgagcgt ataaagggaa ggcttgacag tgctatagca    2040
aagacttttt ctattcgcag cgctagaggc cggtctattt atgatatatt ctcacagtca    2100
gaaattggag tgctggctcg tataaaaaaa agacgagcaa cgttctctga gaatcaaaat    2160
tctttctttg atgccttccc aacaggatac aaggatattg atgataaagg agttatctta    2220
gctaaaggta atttcgtgat tatagcagct aggccatcta tagggaaaac tgctttagct    2280
atagacatgg cgataaatct tgcggttact caacagcgta gagttggttt cctatctcta    2340
gaaatgagcg caggtcaaat tgttgagcgg attattgcta atttaacagg aatatctggt    2400
gaaaaattac aaagaggtgga tctctctaaa gaagaattat tccgagtaga agaagctgga    2460
gaaacagtta gagaatcaca ttttatatc tgcagtgata gtcagtataa gcttaattta    2520
atcgcgaatc agatccggtt gctgagaaaa gaagatcgag tagacgtaat atttatcgat    2580
tacttgcagt tgatcaactc atcggttgga gaaaatcgtc aaaatgaaat agcagatata    2640
tctagaacct taagaggttt agcctcagag ctaaacattc ctatagtttg cttatcccaa    2700
ctatctagaa aagttgagga tagagcaaat aaagttccca tgctttcaga tttgcgagac    2760
agcggtcaaa tagagcaaga cgcagatgtg attttgttta tcaataggaa ggaatcgtct    2820
tctaattgtg agataactgt tgggaaaaat agacatggat cggttttctc ttcggtatta    2880
catttcgatc caaaaattag taaattctcc gctattaaaa aagtatggta aattatagta    2940
actgccactt catcaaaagt cctatccacc ttgaaaatca gaagtttgga agaagacctg    3000
gtcaatctat taagatatct cccaaattgg ctcaaaatgg gatggtagaa gttataggtc    3060
ttgattttct ttcatctcat taccatgcat tagcagctat ccaaagattg ctgactgcaa    3120
cgaattacaa ggggaacaca aaaggggttg ttttatccag agaatcaaat agttttcaat    3180
ttgaaggatg gataccaaga atccgtttta caaaaactga attcttagag gcttatggag    3240
ttaagcggta taaacatcc agaaataagt atgagtttag tggaaaagaa gctgaaactg    3300
ctttagaagc cttataccat ttaggacatc aaccgttttt aatagtggca actagaactc    3360
gatggactaa tggaacacaa atagtagacc gttaccaaac tctttctccg atcattagga    3420
tttacgaagg atgggaaggt ttaactgacg aagaaaatat agatatagac ttaacacctt    3480
ttaattcacc atctacacgg aaacataaag ggttcgttgt agagccatgt cctatcttgg    3540
tagatcaaat agaatcctac tttgtaatca agcctgcaaa tgtataccaa gaaataaaaa    3600
tgcgcttccc aaatgcatca agtatgctt acacatttat cgactgggtg attacagcag    3660
ctgcgaaaaa gagacgaaaa ttaactaagg ataattcttg gccagaaaac ttgttcttaa    3720
acgttaacgt taaagtctt gcatatattt taaggatgaa tcggtacatt tgtacaagga    3780
actgaaaaaa aatcgagtta gctatcgata aatgtataga aatcgccatt cagcttggtt    3840
ggttatctag aagaaaacgc attgaatttc tggattcttc taaactctct aaaaaagaaa    3900
ttctatatct aaataaagag cgttttgaag aaataaccaa gaaatctaaa gaacaaatgg    3960
aacaattaga acaagaatct attaattaat agcaaacttg aaactaaaaa cctaattttat    4020
ttaaagctca aaataaaaaa gagttttaaa atgggaaatt ctggttttta tttgtataac    4080
```

```
actcaaaact gcgtctttgc tgataatatc aaagttgggc aaatgacaga gccgctcaag    4140
gaccagcaaa taatccttgg gacaacatca acacctgtcg cagccaaaat gacagcttct    4200
gatggaatat ctttaacagt ctccaataat ccatcaacca atgcttctat tacaattggt    4260
ttggatgcgg aaaaagctta ccagcttatt ctagaaaagt tgggagatca aattcttggt    4320
ggaattgctg atactattgt tgatagtaca gtccaagata ttttagacaa aatcacaaca    4380
gacccttctc taggtttgtt gaaagctttt aacaactttc ccaatcacta ataaaattca    4440
atgcaacggg ttattcactc ccaggaacat tgaaacttta ttaggaggaa ctgaaatagg    4500
aaaattcaca gtcacaccca aaagctctgg gagcatgttc ttagtctcag cagatattat    4560
tgcatcaaga atggaaggcg gcgttgttct agctttggta cgagaaggtg attctaagcc    4620
ctacgcgatt agttatggat actcatcagg cgttcctaat ttatgtagtc taagaaccag    4680
aattattaat acaggattga ctccgacaac gtattcatta cgtgtaggcg gtttagaaag    4740
cggtgtggta tgggttaatg ccctttctaa tggcaatgat attttaggaa taacaaatac    4800
ttctaatgta tctttttgg aggtaatacc tcaaacaaac gcttaaacaa ttttattgg     4860 attttctta taggttttat atttagaaa aaaagttcga attacggggt tgttatgca      4920 aaataaagc aaagtgaggg acgattttat taaaattgtt aaagatgtga aaaagattt      4980 ccccgaatta gacctaaaaa tacgagtaaa caaggaaaaa gtaactttct taaattctcc    5040
cttagaactc taccataaaa gtgtctcact aattctagga ctgcttcaac aaatagaaaa    5100
ctctttagga ttattcccag actctcctgt tcttgaaaaa ttagaggata acagtttaaa    5160
gctaaaaaag gctttgatta tgcttatctt gtctagaaaa gacatgtttt ccaaggctga    5220
atagataact tactctaacg ttggagttga tttgcacacc ttagtttttt gctcttttaa    5280
gggaggaact ggaaaaacaa cactttctct aaacgtggga tgcaacttgg cccaattttt    5340
agggaaaaaa gtgttacttg ctgacctaga cccgcaatcc aatttatctt ctggattggg    5400
ggctagtgtc agaagtaacc aaaaaggctt acacgacata gtatacacat caaacgattt    5460
aaaatcaatc atttgcgaaa caaaaaaga tagtgtggac ctaattcctg catcatttt     5520 atccgaacag tttagagaat tggatattca tagaggacct agtaacaact taagttatt    5580 tctgaatgag tactgcgctc ctttttatga catctgcata atagacactc cacctagcct    5640
aggagggtta acgaaagaag cttttgttgc aggagacaaa ttaattgctt gtttaactcc    5700 agaaccttt tctattctag ggttacaaaa gatacgtgaa ttcttaagtt cggtcggaaa    5760
acctgaagaa gaacacattc ttggaatagc tttgtctttt tgggatgatc gtaactcgac    5820
taaccaaatg tatatagaca ttatcgagtc tatttacaaa aacaagcttt tttcaacaaa    5880
aattcgtcga gatatttctc tcagccgttc tcttcttaaa gaagattctg tagctaatgt    5940
ctatccaaat tctagggccg cagaagatat tctgaagtta acgcatgaaa tagcaaatat    6000
tttgcatatc gaatatgaac gagattactc tcagaggaca acgtgaacaa actaaaaaaa    6060
gaagcgaatg tcttttttaa aaaaaatcaa actgccgctt ctttagattt taagaagacg    6120
cttccttcca ttgaactatt ctcagcaact ttgaattctg aggaaagtca gagtttggat    6180
caattatttt tatcagagtc ccaaaactat tcggatgaag aattttatca agaagacatc    6240
ctagcggtaa aactgcttac tggtcagata aaatccatac agaagcaaca cgtacttctt    6300
ttaggagaaa aaatctataa tgctagaaaa atcctgagta aggatcactt ctcctcaaca    6360 acttttcat cttggataga gttagttttt agaactaagt cttctgctta caatgctctt    6420
```

```
gcatattacg agcttttat aaacctcccc aaccaaactc tacaaaaaga gtttcaatcg    6480
atcccctata aatccgcata tattttggcc gctagaaaag gcgatttaaa aaccaaggtc    6540
gatgtgatag ggaaagtatg tggaatgtcg aactcatcgg cgataagggt gttggatcaa    6600
tttcttcctt catctagaaa caaagacgtt agagaaacga tagataagtc tgattcagag    6660
aagaatcgcc aattatctga tttcttaata gagatacttc gcatcatgtg ttccggagtt    6720
tctttgtcct cctataacga aaatcttcta caacagcttt ttgaactttt taagcaaaag    6780
agctgatcct ccgtcagctc atatatatat ctattatata tatatattta gggatttgat    6840
tttacgagag agatttgcaa ctcttggtgg tagactttgc aactcttggt ggtagacttt    6900
gcaactcttg gtggtagact ttgcaactct tggtggtaga cttggtcata atggactttt    6960
gttgaaaaat ttcttaaaat cttagagctc cgattttgaa tagctttggt taagaaaatg    7020
ggctcgatgg cttccataa aagtaggttg ttcttaactt ttggggacgc gtcggaaatt    7080
tggttatcta ctttatctca tctaactaga aaaaattatg cgtctgggat taactttctt    7140
gtttctttag agattctgga tttatcggaa accttgataa aggctatttc tcttgaccac    7200
agcgaatctt tgtttaaaat caagtctcta gatgttttta atggaaaagt cgtttcagag    7260
gcctctaaac aggctagagc ggcatgctac atatctttca caaagttttt gtatagattg    7320
accaagggat atattaaacc cgctattcca ttgaaagatt ttggaaacac tacatttttt    7380
aaaatccgag acaaaatcaa aacagaatcg atttctaagc aggaatggac agttttttt    7440 gaagcgctcc ggatagtgaa ttatagagac tatttaatcg gtaaattgat tgtacaag     7498
```